US010500266B2

United States Patent
Mason et al.

(10) Patent No.: US 10,500,266 B2
(45) Date of Patent: *Dec. 10, 2019

(54) INFLUENZA VIRUS REASSORTMENT

(71) Applicants: Seqirus UK Limited, Berkshire (GB); Synthetic Genomics, Inc., La Jolla, CA (US)

(72) Inventors: Peter Mason, Cambridge, MA (US); Philip Ralph Dormitzer, Cambridge, MA (US); Heidi Trusheim, Marburg (DE); Pirada Suphaphiphat, Cambridge, MA (US)

(73) Assignees: Seqirus UK Limited, Berkshire (GB); Synthetic Genomics, Inc., La Lolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/621,270

(22) Filed: Jun. 13, 2017

(65) Prior Publication Data

US 2017/0326227 A1   Nov. 16, 2017

Related U.S. Application Data

(63) Continuation of application No. 14/648,886, filed as application No. PCT/EP2013/075294 on Dec. 2, 2013, now Pat. No. 9,708,585.

(60) Provisional application No. 61/732,809, filed on Dec. 3, 2012.

(51) Int. Cl.
| | |
|---|---|
| *A61K 39/145* | (2006.01) |
| *C12N 7/00* | (2006.01) |
| *A61K 39/12* | (2006.01) |
| *A61K 39/00* | (2006.01) |

(52) U.S. Cl.
CPC ............ *A61K 39/145* (2013.01); *A61K 39/12* (2013.01); *C12N 7/00* (2013.01); *A61K 2039/5252* (2013.01); *C12N 2760/16121* (2013.01); *C12N 2760/16134* (2013.01); *C12N 2760/16151* (2013.01); *C12N 2760/16152* (2013.01)

(58) Field of Classification Search
None
See application file for complete search history.

(56) References Cited

U.S. PATENT DOCUMENTS

| | | | |
|---|---|---|---|
| 9,708,585 B2 * | 7/2017 | Mason | A61K 39/145 |
| 2007/0231348 A1 | 10/2007 | Kawaoka et al. | |
| 2011/0123559 A1 | 5/2011 | Jin | |

FOREIGN PATENT DOCUMENTS

| | | |
|---|---|---|
| WO | WO 2008/157419 A2 | 12/2008 |
| WO | WO 2010/070098 A1 | 6/2010 |
| WO | WO 2010/077986 A2 | 7/2010 |
| WO | WO 2010/151673 A1 | 12/2010 |
| WO | WO 2011/145081 A1 | 11/2011 |
| WO | WO 2012/007380 A1 | 1/2012 |

OTHER PUBLICATIONS de Wit et al., "Efficient generation and growth of influenza virus A/PR/8/34 from eight cDNA fragments," Virus Res, 103(1-2):155-161, (2004).
GenBank Accession # ACP41958, polymerase PB1 [Influenza A virus (A/California/07/2009(H1N1))], Jun. 1, 2009.
GenBank Accession # NP_040978, matrix protein 1 [Influenza A virus (A/Puerto Rico/8/1934(H1N1))], Jul. 16, 2008.
GenBank Accesssion # P03428, RecName: Full=Polymerase basic protein 2; AltName: Full=RNA-directed RNA polymerase subunit P3, Jun. 16, 2009.
GenBank Accession # P17042, RecName: Full=Non-structural protein 1; Short=NS1; AltName: Full=NS1A., Jun. 16, 2009.
GenBank Accession # P03466, RecName: Full=Nucleoprotein; AltName: Fuii=Nucleocapsid protein; Short=Protein N., Jun. 16, 2009.
GenBank Accession # P03433, RecName: Full=Polymerase acidic protein; AltName: Full=RNA-directed RNA polymerase subunit P2., Jul. 28, 2009.
International Search Report and Written Opinion for PCT Patent Application No. PCT/EP2013/075294, dated Jun. 4, 2014, 19 pages.
International Preliminary Report on Patentability for PCT Patent Application No. PCT/EP2013/075294, dated Jun. 18, 2015, 13 pages.
NIBSC Influenza Reagent, Influenza Virus Infectious NYMC X-179A, Nov. 11, 2009.
Abt et al., "Improvement of H5N1 influenza vaccine viruses: influence of internal gene segments of avian and human origin on production and hemagglutinin content," Vaccine, 29(32):5153-5162, (2011).
Fulvini et al., "Gene constellation of influenza A virus reassortants with high growth phenotype prepared as seed candidates for vaccine production," PLoS One, 6(6):e20823, (2011).
Phuah et al., "Genbank Accession No. CY123396, Influenza A Virus (A/Singapore/ON1074/2009(H1N1) Polymerase PB1 Gene, Complete cds; and PB1-F2 Gene, Complete Sequence", Available Online at <http://www.ncbi.nlm.nih.gov/nuccore/CY123396#sequence_393709993>, 2012, 2 pages.
Wanitchang et al., "Enhancement of reverse genetics-derived swine-origin H1N1 influenza virus seed vaccine growth by inclusion of indigenous polymerase PB1 protein," Virus Res, 147(1):145-148, (2010).

* cited by examiner

*Primary Examiner* — Benjamin P Blumel
(74) *Attorney, Agent, or Firm* — Finnegan, Henderson, Farabow, Garrett & Dunner, LLP

(57) ABSTRACT

New influenza donor strains for the production of reassortant influenza A viruses are provided.

23 Claims, 9 Drawing Sheets

Specification includes a Sequence Listing.

SEQUENCE LISTING

<160> NUMBER OF SEQ ID NOS: 32

<210> SEQ ID NO 1
<211> LENGTH: 716
<212> TYPE: PRT
<213> ORGANISM: Unknown
<220> FEATURE:
<223> OTHER INFORMATION: Influenza

<400> SEQUENCE: 1

```
Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
            20                  25                  30

Asn Lys Phe Ala Ala Ile Cys Thr His Leu Glu Val Cys Phe Met Tyr
        35                  40                  45

Ser Asp Phe His Phe Ile Asn Glu Gln Gly Glu Ser Ile Ile Val Glu
    50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
        195                 200                 205

Gly Thr Met Arg Lys Leu Ala Asp Gln Ser Leu Pro Pro Asn Phe Ser
    210                 215                 220

Ser Leu Glu Asn Phe Arg Ala Tyr Val Asp Gly Phe Glu Pro Asn Gly
225                 230                 235                 240
```

-continued

```
Tyr Ile Glu Gly Lys Leu Ser Gln Met Ser Lys Glu Val Asn Ala Arg
            245                 250                 255
Ile Glu Pro Phe Leu Lys Thr Thr Pro Arg Pro Leu Arg Leu Pro Asn
        260                 265                 270
Gly Pro Pro Cys Ser Gln Arg Ser Lys Phe Leu Leu Met Asp Ala Leu
    275                 280                 285
Lys Leu Ser Ile Glu Asp Pro Ser His Glu Gly Gly Ile Pro Leu
290                 295                 300
Tyr Asp Ala Ile Lys Cys Met Arg Thr Phe Phe Gly Trp Lys Glu Pro
305                 310                 315                 320
Asn Val Val Lys Pro His Glu Lys Gly Ile Asn Pro Asn Tyr Leu Leu
                325                 330                 335
Ser Trp Lys Gln Val Leu Ala Glu Leu Gln Asp Ile Glu Asn Glu Glu
            340                 345                 350
Lys Ile Pro Lys Thr Lys Asn Met Lys Lys Thr Ser Gln Leu Lys Trp
        355                 360                 365
Ala Leu Gly Glu Asn Met Ala Pro Glu Lys Val Asp Phe Asp Asp Cys
    370                 375                 380
Lys Asp Val Gly Asp Leu Lys Gln Tyr Asp Ser Asp Glu Pro Glu Leu
385                 390                 395                 400
Arg Ser Leu Ala Ser Trp Ile Gln Asn Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu His Ile Ala Ser Met Arg Arg Asn Tyr Phe Thr Ser
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
Asp Pro Arg Leu Glu Pro His Lys Trp Glu Lys Tyr Cys Val Leu Glu
    530                 535                 540
Ile Gly Asp Met Leu Ile Arg Ser Ala Ile Gly Gln Val Ser Arg Pro
545                 550                 555                 560
Met Phe Leu Tyr Val Arg Thr Asn Gly Thr Ser Lys Ile Lys Met Lys
                565                 570                 575
Trp Gly Met Glu Met Arg Arg Cys Leu Leu Gln Ser Leu Gln Gln Ile
            580                 585                 590
Glu Ser Met Ile Glu Ala Glu Ser Ser Val Lys Glu Lys Asp Met Thr
        595                 600                 605
Lys Glu Phe Phe Glu Asn Lys Ser Glu Thr Trp Pro Ile Gly Glu Ser
    610                 615                 620
Pro Lys Gly Val Glu Glu Ser Ser Ile Gly Lys Val Cys Arg Thr Leu
625                 630                 635                 640
Leu Ala Lys Ser Val Phe Asn Ser Leu Tyr Ala Ser Pro Gln Leu Glu
                645                 650                 655
```

```
Gly Phe Ser Ala Glu Ser Arg Lys Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715

<210> SEQ ID NO 2
<211> LENGTH: 757
<212> TYPE: PRT
<213> ORGANISM: Unknown
<220> FEATURE:
<223> OTHER INFORMATION: Influenza

<400> SEQUENCE: 2

Met Asp Val Asn Pro Thr Leu Leu Phe Leu Lys Val Pro Thr Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Met Gly Lys Lys
        195                 200                 205

Lys Gln Arg Leu Asn Lys Arg Ser Tyr Leu Ile Arg Ala Leu Thr Leu
210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
290                 295                 300
```

```
Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
            325                 330                 335

Leu Ser Ile Ala Pro Ile Met Phe Ser Asn Lys Met Ala Arg Leu Gly
        340                 345                 350

Lys Gly Tyr Met Phe Glu Ser Lys Ser Met Lys Leu Arg Thr Gln Ile
    355                 360                 365

Pro Ala Glu Met Leu Ala Ser Ile Asp Leu Lys Tyr Phe Asn Asp Ser
370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Gly Met Phe Asn Met Leu Ser
            405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
```

```
                    725                 730                 735

Lys Glu Glu Phe Thr Glu Ile Met Lys Ile Cys Ser Thr Ile Glu Glu
            740                 745                 750

Leu Arg Arg Gln Lys
            755

<210> SEQ ID NO 3
<211> LENGTH: 759
<212> TYPE: PRT
<213> ORGANISM: Unknown
<220> FEATURE:
<223> OTHER INFORMATION: Influenza

<400> SEQUENCE: 3

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Ile Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Arg Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
```

```
                    325                 330                 335
Ser Val Lys Arg Glu Glu Val Leu Thr Gly Asn Leu Gln Thr Leu
                340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Leu Ile Gln Leu
        370                 375                 380
Ile Val Ser Gly Arg Asp Glu Gln Ser Ile Ala Glu Ala Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
            420                 425                 430
Gln Leu Leu Arg His Phe Gln Lys Asp Ala Arg Val Leu Phe Gln Asn
        435                 440                 445
Trp Gly Val Glu Pro Ile Asp Asn Val Met Gly Met Ile Gly Ile Leu
        450                 455                 460
Pro Asp Met Thr Pro Ser Ile Glu Met Ser Met Arg Gly Val Arg Ile
465                 470                 475                 480
Ser Lys Met Gly Val Asp Glu Tyr Ser Ser Thr Glu Arg Val Val Val
                485                 490                 495
Ser Ile Asp Arg Phe Leu Arg Ile Arg Asp Gln Arg Gly Asn Val Leu
            500                 505                 510
Leu Ser Pro Glu Glu Val Ser Glu Thr Gln Gly Thr Glu Lys Leu Thr
        515                 520                 525
Ile Thr Tyr Ser Ser Ser Met Met Trp Glu Ile Asn Gly Pro Glu Ser
        530                 535                 540
Val Leu Val Asn Thr Tyr Gln Trp Ile Ile Arg Asn Trp Glu Thr Val
545                 550                 555                 560
Lys Ile Gln Trp Ser Gln Asn Pro Thr Met Leu Tyr Asn Lys Met Glu
                565                 570                 575
Phe Glu Pro Phe Gln Ser Leu Val Pro Lys Ala Ile Arg Gly Gln Tyr
            580                 585                 590
Ser Gly Phe Val Arg Thr Leu Phe Gln Gln Met Arg Asp Val Leu Gly
        595                 600                 605
Thr Phe Asp Thr Ala Gln Ile Ile Lys Leu Leu Pro Phe Ala Ala Ala
        610                 615                 620
Pro Pro Lys Gln Ser Arg Met Gln Phe Ser Ser Phe Thr Val Asn Val
625                 630                 635                 640
Arg Gly Ser Gly Met Arg Ile Leu Val Arg Gly Asn Ser Pro Val Phe
                645                 650                 655
Asn Tyr Asn Lys Ala Thr Lys Arg Leu Thr Val Leu Gly Lys Asp Ala
            660                 665                 670
Gly Thr Leu Thr Glu Asp Pro Asp Glu Gly Thr Ala Gly Val Glu Ser
        675                 680                 685
Ala Val Leu Arg Gly Phe Leu Ile Leu Gly Lys Glu Asp Lys Arg Tyr
        690                 695                 700
Gly Pro Ala Leu Ser Ile Asn Glu Leu Ser Asn Leu Ala Lys Gly Glu
705                 710                 715                 720
Lys Ala Asn Val Leu Ile Gly Gln Gly Asp Val Val Leu Val Met Lys
                725                 730                 735
Arg Lys Arg Asp Ser Ser Ile Leu Thr Asp Ser Gln Thr Ala Thr Lys
            740                 745                 750
```

```
Arg Ile Arg Met Ala Ile Asn
        755

<210> SEQ ID NO 4
<211> LENGTH: 498
<212> TYPE: PRT
<213> ORGANISM: Unknown
<220> FEATURE:
<223> OTHER INFORMATION: Influenza

<400> SEQUENCE: 4

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
    290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350
```

```
Leu Pro Arg Gly Lys Leu Ser Thr Arg Gly Val Gln Ile Ala Ser Asn
            355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 5
<211> LENGTH: 252
<212> TYPE: PRT
<213> ORGANISM: Unknown
<220> FEATURE:
<223> OTHER INFORMATION: Influenza

<400> SEQUENCE: 5

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
                20                  25                  30

Ala Gly Lys Asn Thr Asp Leu Glu Val Leu Met Glu Trp Leu Lys Thr
            35                  40                  45

Arg Pro Ile Leu Ser Pro Leu Thr Lys Gly Ile Leu Gly Phe Val Phe
        50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

Val Lys Leu Tyr Arg Lys Leu Lys Arg Glu Ile Thr Phe His Gly Ala
            100                 105                 110

Lys Glu Ile Ser Leu Ser Tyr Ser Ala Gly Ala Leu Ala Ser Cys Met
        115                 120                 125

Gly Leu Ile Tyr Asn Arg Met Gly Ala Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205
```

Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 6
<211> LENGTH: 230
<212> TYPE: PRT
<213> ORGANISM: Unknown
<220> FEATURE:
<223> OTHER INFORMATION: Influenza

<400> SEQUENCE: 6

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Lys Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Asp Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Pro Pro Leu Thr Pro Lys Gln Lys Arg Glu Met Ala Gly
    210                 215                 220

Thr Ile Arg Ser Glu Val
225                 230

<210> SEQ ID NO 7
<211> LENGTH: 565
<212> TYPE: PRT
<213> ORGANISM: Unknown
<220> FEATURE:
<223> OTHER INFORMATION: Influenza

<400> SEQUENCE: 7

Met Lys Ala Asn Leu Leu Val Leu Leu Cys Ala Leu Ala Ala Ala Asp
1               5                   10                  15

Ala Asp Thr Ile Cys Ile Gly Tyr His Thr Asn Asn Ser Thr Asp Thr
            20                  25                  30

```
Val Asp Thr Val Leu Glu Lys Asn Val Thr Val Thr His Ser Val Asn
         35                  40                  45
Leu Leu Glu Asp Ser His Asn Gly Lys Leu Cys Arg Leu Lys Gly Ile
 50                  55                  60
Ala Pro Leu Gln Leu Gly Lys Cys Asn Ile Ala Gly Trp Leu Leu Gly
 65                  70                  75                  80
Asn Pro Glu Cys Asp Pro Leu Leu Pro Val Arg Ser Trp Ser Tyr Ile
             85                  90                  95
Val Glu Thr Pro Asn Ser Glu Asn Gly Ile Cys Tyr Pro Gly Asp Phe
            100                 105                 110
Ile Asp Tyr Glu Glu Leu Arg Glu Gln Leu Ser Ser Val Ser Ser Phe
            115                 120                 125
Glu Arg Phe Glu Ile Phe Pro Lys Glu Ser Ser Trp Pro Asn His Asn
        130                 135                 140
Thr Asn Gly Val Thr Ala Ala Cys Ser His Glu Gly Lys Ser Ser Phe
145                 150                 155                 160
Tyr Arg Asn Leu Leu Trp Leu Thr Glu Lys Glu Gly Ser Tyr Pro Lys
                165                 170                 175
Leu Lys Asn Ser Tyr Val Asn Lys Lys Gly Lys Glu Val Leu Val Leu
            180                 185                 190
Trp Gly Ile His His Pro Pro Asn Ser Lys Glu Gln Gln Asn Leu Tyr
        195                 200                 205
Gln Asn Glu Asn Ala Tyr Val Ser Val Val Thr Ser Asn Tyr Asn Arg
        210                 215                 220
Arg Phe Thr Pro Glu Ile Ala Glu Arg Pro Lys Val Arg Asp Gln Ala
225                 230                 235                 240
Gly Arg Met Asn Tyr Tyr Trp Thr Leu Leu Lys Pro Gly Asp Thr Ile
                245                 250                 255
Ile Phe Glu Ala Asn Gly Asn Leu Ile Ala Pro Met Tyr Ala Phe Ala
            260                 265                 270
Leu Ser Arg Gly Phe Gly Ser Gly Ile Ile Thr Ser Asn Ala Ser Met
        275                 280                 285
His Glu Cys Asn Thr Lys Cys Gln Thr Pro Leu Gly Ala Ile Asn Ser
        290                 295                 300
Ser Leu Pro Tyr Gln Asn Ile His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Ile Asp Gly Trp Tyr Gly Tyr His
        355                 360                 365
His Gln Asn Glu Gln Gly Ser Gly Tyr Ala Ala Asp Gln Lys Ser Thr
        370                 375                 380
Gln Asn Ala Ile Asn Gly Ile Thr Asn Lys Val Asn Thr Val Ile Glu
385                 390                 395                 400
Lys Met Asn Ile Gln Phe Thr Ala Val Gly Lys Glu Phe Asn Lys Leu
                405                 410                 415
Glu Lys Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
```

Arg Thr Leu Glu Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
                515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 8
<211> LENGTH: 454
<212> TYPE: PRT
<213> ORGANISM: Unknown
<220> FEATURE:
<223> OTHER INFORMATION: Influenza

<400> SEQUENCE: 8

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
                20                  25                  30

Trp Ile Ser His Ser Ile Gln Thr Gly Ser Gln Asn His Thr Gly Ile
            35                  40                  45

Cys Asn Gln Asn Ile Ile Thr Tyr Lys Asn Ser Thr Trp Val Lys Asp
        50                  55                  60

Thr Thr Ser Val Ile Leu Thr Gly Asn Ser Ser Leu Cys Pro Ile Arg
65                  70                  75                  80

Gly Trp Ala Ile Tyr Ser Lys Asp Asn Ser Ile Arg Ile Gly Ser Lys
                85                  90                  95

Gly Asp Val Phe Val Ile Arg Glu Pro Phe Ile Ser Cys Ser His Leu
                100                 105                 110

Glu Cys Arg Thr Phe Phe Leu Thr Gln Gly Ala Leu Leu Asn Asp Lys
            115                 120                 125

His Ser Ser Gly Thr Val Lys Asp Arg Ser Pro Tyr Arg Ala Leu Met
        130                 135                 140

Ser Cys Pro Val Gly Glu Ala Pro Ser Pro Tyr Asn Ser Arg Phe Glu
145                 150                 155                 160

Ser Val Ala Trp Ser Ala Ser Ala Cys His Asp Gly Met Gly Trp Leu
                165                 170                 175

Thr Ile Gly Ile Ser Gly Pro Asp Asn Gly Ala Val Ala Val Leu Lys
                180                 185                 190

Tyr Asn Gly Ile Ile Thr Glu Thr Ile Lys Ser Trp Arg Lys Lys Ile
            195                 200                 205

Leu Arg Thr Gln Glu Ser Glu Cys Ala Cys Val Asn Gly Ser Cys Phe
        210                 215                 220

Thr Ile Met Thr Asp Gly Pro Ser Asp Gly Leu Ala Ser Tyr Lys Ile
225                 230                 235                 240

| | | | | | | | | | | | | |
|---|---|---|---|---|---|---|---|---|---|---|---|---|
|Phe|Lys|Ile|Glu|Lys|Gly|Lys|Val|Thr|Lys|Ser|Ile|Glu|Leu|Asn|Ala|
| | | |245| | | |250| | | |255| |

Phe Lys Ile Glu Lys Gly Lys Val Thr Lys Ser Ile Glu Leu Asn Ala
                245                 250                 255

Pro Asn Ser His Tyr Glu Glu Cys Ser Cys Tyr Pro Thr Asp Lys
            260                 265                 270

Val Met Cys Val Cys Arg Asp Asn Trp His Gly Ser Asn Arg Pro Trp
        275                 280                 285

Val Ser Phe Asp Gln Asn Leu Asp Tyr Gln Ile Gly Tyr Ile Cys Ser
        290                 295                 300

Gly Val Phe Gly Asp Asn Pro Arg Pro Glu Asp Gly Thr Gly Ser Cys
305                 310                 315                 320

Gly Pro Val Tyr Val Asp Gly Ala Asn Gly Val Lys Gly Phe Ser Tyr
                325                 330                 335

Arg Tyr Gly Asn Gly Val Trp Ile Gly Arg Thr Lys Ser His Ser Ser
                340                 345                 350

Arg His Gly Phe Glu Met Ile Trp Asp Pro Asn Gly Trp Thr Glu Thr
                355                 360                 365

Asp Ser Lys Phe Ser Val Arg Gln Asp Val Val Ala Met Thr Asp Trp
            370                 375                 380

Ser Gly Tyr Ser Gly Ser Phe Val Gln His Pro Glu Leu Thr Gly Leu
385                 390                 395                 400

Asp Cys Met Arg Pro Cys Phe Trp Val Glu Leu Ile Arg Gly Arg Pro
                405                 410                 415

Lys Glu Lys Thr Ile Trp Thr Ser Ala Ser Ser Ile Ser Phe Cys Gly
                420                 425                 430

Val Asn Ser Asp Thr Val Asp Trp Ser Trp Pro Asp Gly Ala Glu Leu
            435                 440                 445

Pro Phe Ser Ile Asp Lys
    450

<210> SEQ ID NO 9
<211> LENGTH: 2233
<212> TYPE: DNA
<213> ORGANISM: Unknown
<220> FEATURE:
<223> OTHER INFORMATION: Influenza

<400> SEQUENCE: 9
agcgaaagca ggtactgatc caaaatggaa gattttgtgc gacaatgctt caatccgatg      60
attgtcgagc ttgcggaaaa acaatgaaa gagtatgggg aggacctgaa atcgaaaca      120 aacaaatttg cagcaatatg cactcacttg gaagtatgct tcatgtattc agattttcac      180
ttcatcaatg agcaaggcga gtcaataatc gtagaacttg gtgatccaaa tgcacttttg      240
aagcacagat ttgaaataat cgagggaaga gatcgcacaa tggcctggac agtagtaaac      300
agtatttgca cactacagg ggctgagaaa ccaaagtttc taccagattt gtatgattac      360
aaggagaata gatttatcga aattggagta caaggagag aagttcacat atactatctg      420
gaaaaggcca ataaaattaa atctgagaaa acacacatcc acattttctc gttcactggg      480
gaagaaatgg ccacaaaggc agactacact ctcgatgaag aaagcagggc taggatcaaa      540
accagactat tcaccataag acaagaaatg gccagcagag gcctctggga ttcctttcgt      600
cagtccgaga gaggagaaga gacaattgaa gaaaggtttg aaatcacagg aacaatgcgc      660
aagcttgccg accaaagtct cccgccgaac ttctccagcc ttgaaaattt tagagcctat      720
gtggatggat tcgaaccgaa cggctacatt gagggcaagc tgtctcaaat gtccaaagaa      780
gtaaatgcta gaattgaacc ttttttgaaa acaacaccac gaccacttag acttccgaat      840

```
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaagggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaagggg gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag gagatatgct tataagaagt   1680
gccataggcc aggtttcaag gcccatgttc ttgtatgtga gaacaaatgg aacctcaaaa   1740
attaaaatga atgggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aaggagtgga ggaaagttcc   1920
attgggaagg tctgcaggac tttattagca aagtcggtat caacagcttg tatgcatct   1980 ccacaactag aaggattttc agctgaatca agaaaactgc ttcttatcgt tcaggctctt   2040
agggacaacc ttgaacctgg gacctttgat cttgggggggc tatatgaagc aattgaggag   2100
tgcctgatta atgatccctg ggttttgctt aatgcttctt ggttcaactc cttccttaca   2160
catgcattga gttagttgtg gcagtgctac tatttgctat ccatactgtc caaaaagta   2220 ccttgtttct act                                                      2233
```

<210> SEQ ID NO 10
<211> LENGTH: 2341
<212> TYPE: DNA
<213> ORGANISM: Unknown
<220> FEATURE:
<223> OTHER INFORMATION: Influenza

<400> SEQUENCE: 10

```
agcgaaagca ggcaaaccat ttgaatggat gtcaatccga ccttactttt cttaaaagtg     60
ccaacacaaa atgctataag cacaactttc cctatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga acgatggag    360 gttgttcagc aaacacgagt agacaagctg acacaaggcc gacagaccta tgactggact    420
ctaaatagaa accaacctgc tgcaacagca ttggccaaca atagaagt gttcagatca    480 aatggcctca cggccaatga gtctggaagg ctcatagact ccttaagga tgtaatggag    540 tcaatgaaca aagaagaaat ggggatcaca actcattttc agagaaagag acgggtgaga    600
```

-continued

| | |
|---|---|
| gacaatatga ctaagaaaat gataacacag agaacaatgg gtaaaagaa gcagagattg | 660 |
| aacaaaagga gttatctaat tagagcattg accctgaaca caatgaccaa agatgctgag | 720 |
| agagggaagc taaacggag agcaattgca accccaggga tgcaaataag ggggtttgta | 780 |
| tactttgttg agacactggc aaggagtata tgtgagaaac ttgaacaatc agggttgcca | 840 |
| gttggaggca atgagaagaa agcaaagttg gcaaatgttg taaggaagat gatgaccaat | 900 |
| tctcaggaca ccgaactttc tttcaccatc actggagata caccaaatg gaacgaaaat | 960 |
| cagaatcctc ggatgttttt ggccatgatc acatatatga ccagaaatca gcccgaatgg | 1020 |
| ttcagaaatg ttctaagtat tgctccaata atgttctcaa acaaaatggc gagactggga | 1080 |
| aagggtata tgtttgagag caagagtatg aaacttagaa ctcaaatacc tgcagaaatg | 1140 |
| ctagcaagca tcgatttgaa atatttcaat gattcaacaa gaagaagat tgaaaaaatc | 1200 |
| cgaccgctct aatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactactt actggtggga tggtcttcaa tcctctgacg atttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagtttt tctatcgtta tgggtttgtt gccaatttca gcatggagct tcccagtttt | 1560 |
| ggggtgtctg ggatcaacga gtcagcggac atgagtattg gagttactgt catcaaaaac | 1620 |
| aatatgataa acaatgatct tggtccagca acagctcaaa tggcccttca gttgttcatc | 1680 |
| aaagattaca ggtacacgta ccgatgccat agaggtgaca cacaaataca aacccgaaga | 1740 |
| tcatttgaaa taagaaact gtgggagcaa accgttcca agctggact gctggtctcc | 1800 |
| gacgaggcc caatttata caacattaga aatctccaca ttcctgaagt ctgcctaaaa | 1860 |
| tgggaattga tggatgagga ttaccagggg cgtttatgca acccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatccccaa agaaatcga | 2040 |
| tccatcttga atacaagtca agaggagta cttgaggatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 11
<211> LENGTH: 2341
<212> TYPE: DNA
<213> ORGANISM: Unknown
<220> FEATURE:
<223> OTHER INFORMATION: Influenza

<400> SEQUENCE: 11

| | |
|---|---|
| agcgaaagca ggtcaattat attcaatatg gaaagaataa agaactaag aaatctaatg | 60 |
| tcgcagtctc gcaccgcga gatactcaca aaaccaccg tggaccatat ggccataatc | 120 |
| aagaagtaca catcaggaag acaggagaag aacccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg gatcagaccg agtgatggta | 300 |

```
tcacctctgg ctgtgacatg gtggaatagg aatggaccaa taacaaatac agttcattat    360
ccaaaaatct acaaaactta ttttgaaaga gtagaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggaaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcagcgatt gaatcctatg   1320
catcaacttt taagacattt tcagaaggat gcgagagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tattggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca agtagaatg    1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
agggattcc tcattctggg caagaagac aagagatatg gccagcact aagcatcaat    2160
gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                   2341
```

<210> SEQ ID NO 12
<211> LENGTH: 1565
<212> TYPE: DNA
<213> ORGANISM: Unknown
<220> FEATURE:
<223> OTHER INFORMATION: Influenza

<400> SEQUENCE: 12

```
agcaaaagca gggtagataa tcactcactg agtgacatca aaatcatggc gtctcaaggc      60
accaaacgat cttacgaaca gatggagact gatggagaac gccagaatgc cactgaaatc     120
agagcatccg tcggaaaaat gattggtgga attggacgat tctacatcca aatgtgcacc     180
gaactcaaac tcagtgatta tgagggacgg ttgatccaaa acagcttaac aatagagaga     240
atggtgctct ctgcttttga cgaaaggaga aataaatacc ttgaagaaca tcccagtgcg     300
ggaaaagatc ctaagaaaac tggaggacct atatacagga gagtaaacgg aaagtggatg     360
agagaactca tcctttatga caaagaagaa ataaggcgaa tctggcgcca agctaataat     420
ggtgacgatg caacggctgg tctgactcac atgatgatct ggcattccaa tttgaatgat     480
gcaacttatc agaggacaag agctcttgtt cgcaccggaa tggatcccag gatgtgctct     540
ctgatgcaag gttcaactct ccctaggagg tctggagccg caggtgctgc agtcaaagga     600
gttggaacaa tggtgatgga attggtcaga atgatcaaac gtgggatcaa tgatcggaac     660
ttctggaggg gtgagaatgg acgaaaaaca agaattgctt atgaaagaat gtgcaacatt     720
ctcaaaggga aatttcaaac tgctgcacaa aaagcaatga tggatcaagt gagagagagc     780
cggaacccag gaatgctgag ttcgaagat ctcacttttc tagcacggtc tgcactcata      840
ttgagagggt cggttgctca caagtcctgc ctgcctgcct gtgtgtatgg acctgccgta     900
gccagtgggt acgactttga agggaggga tactctctag tcggaataga ccctttcaga     960
ctgcttcaaa acagccaagt gtacagccta atcagaccaa atgagaatcc agcacacaag    1020
agtcaactgg tgtggatggc atgccattct gccgcatttg aagatctaag agtattaagc    1080
ttcatcaaag gacgaaggt gctcccaaga gggaagcttt ccactagagg agttcaaatt    1140
gcttccaatg aaaatatgga gactatgaa tcaagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc cttttgacag aacaaccatt    1320
atggcagcat tcaatgggaa tacagagggg agaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
tcttatttct tcggagacaa tgcagaggag tacgacaatt aaagaaaaat accccttgttt    1560
ctact                                                                 1565
```

<210> SEQ ID NO 13
<211> LENGTH: 1027
<212> TYPE: DNA
<213> ORGANISM: Unknown
<220> FEATURE:
<223> OTHER INFORMATION: Influenza

<400> SEQUENCE: 13

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggacggggg atccaaataa     300
catggacaaa gcagttaaac tgtataggaa gctcaagagg gagataacat tccatgggc      360
caaagaaatc tcactcagtt attctgctgg tgcacttgcc agttgtatgg gcctcatata     420
```

```
caacaggatg ggggctgtga ccactgaagt ggcatttggc ctggtatgtg caacctgtga    480
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cactattgcc gcaaatatca tgggatcttg cacttgaca ttgtggattc    840 ttgatcgtct tttttcaaa tgcatttacc gtcgctttaa atacgactg aaaggagggc    900 cttctacgga aggagtgcca aagtctatga gggaagaata tcgaaggaa cagcagagtg    960 ctgtggatgc tgacgatggt cattttgtca gcatagagct ggagtaaaaa actaccttgt   1020
ttctact                                                             1027
```

<210> SEQ ID NO 14
<211> LENGTH: 890
<212> TYPE: DNA
<213> ORGANISM: Unknown
<220> FEATURE:
<223> OTHER INFORMATION: Influenza

<400> SEQUENCE: 14

```
agcaaaagca gggtgacaaa acataatgg atccaaacac tgtgtcaagc tttcaggtag     60
attgctttct ttggcatgtc cgcaaacgag ttgcagacca agaactaggt gatgccccat    120
tccttgatcg gcttcgccga gatcagaaat ccctaagagg aaggggcagt actctcggtc    180
tggacatcaa gacagccaca cgtgctggaa agcagatagt ggagcggatt ctgaaagaag    240
aatccgatga ggcacttaaa atgaccatgg cctctgtacc tgcgtcgcgt tacctaactg    300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gaccggctgg agactctaat attgctaagg ctttcaccg     480 aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga gataacaga gaatagtttt    780 gagcaaataa catttatgca agccttacat ctattgcttg aagtggagca agagataaga    840
actttctcgt ttcagcttat ttagtactaa aaaacaccct gtttctact                890
```

<210> SEQ ID NO 15
<211> LENGTH: 716
<212> TYPE: PRT
<213> ORGANISM: Unknown
<220> FEATURE:
<223> OTHER INFORMATION: Influenza Virus Reassortment

<400> SEQUENCE: 15

Met Glu Asp Phe Val Arg Gln Cys Phe Asn Pro Met Ile Val Glu Leu
1               5                   10                  15

Ala Glu Lys Ala Met Lys Glu Tyr Gly Glu Asp Pro Lys Ile Glu Thr
            20                  25                  30

-continued

```
Asn Lys Phe Ala Ala Ile Cys Thr His Leu Glu Val Cys Phe Met Tyr
         35                  40                  45

Ser Asp Phe His Phe Ile Asp Glu Arg Gly Glu Ser Ile Ile Val Glu
 50                  55                  60

Ser Gly Asp Pro Asn Ala Leu Leu Lys His Arg Phe Glu Ile Ile Glu
 65                  70                  75                  80

Gly Arg Asp Arg Ile Met Ala Trp Thr Val Val Asn Ser Ile Cys Asn
                 85                  90                  95

Thr Thr Gly Val Glu Lys Pro Lys Phe Leu Pro Asp Leu Tyr Asp Tyr
                100                 105                 110

Lys Glu Asn Arg Phe Ile Glu Ile Gly Val Thr Arg Arg Glu Val His
            115                 120                 125

Ile Tyr Tyr Leu Glu Lys Ala Asn Lys Ile Lys Ser Glu Lys Thr His
        130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Ser Leu Trp Asp Ser Phe Arg
                180                 185                 190

Gln Ser Glu Arg Gly Glu Glu Thr Ile Glu Glu Lys Phe Glu Ile Thr
            195                 200                 205

Gly Thr Met Arg Lys Leu Ala Asp Gln Ser Leu Pro Pro Asn Phe Pro
        210                 215                 220

Ser Leu Glu Asn Phe Arg Ala Tyr Val Asp Gly Phe Glu Pro Asn Gly
225                 230                 235                 240

Cys Ile Glu Gly Lys Leu Ser Gln Met Ser Lys Glu Val Asn Ala Lys
                245                 250                 255

Ile Glu Pro Phe Leu Arg Thr Thr Pro Arg Pro Leu Arg Leu Pro Asp
                260                 265                 270

Gly Pro Leu Cys His Gln Arg Ser Lys Phe Leu Leu Met Asp Ala Leu
            275                 280                 285

Lys Leu Ser Ile Glu Asp Pro Ser His Glu Gly Glu Gly Ile Pro Leu
        290                 295                 300

Tyr Asp Ala Ile Lys Cys Met Lys Thr Phe Phe Gly Trp Lys Glu Pro
305                 310                 315                 320

Asn Ile Val Lys Pro His Glu Lys Gly Ile Asn Pro Asn Tyr Leu Met
                325                 330                 335

Ala Trp Lys Gln Val Leu Ala Glu Leu Gln Asp Ile Glu Asn Glu Glu
                340                 345                 350

Lys Ile Pro Arg Thr Lys Asn Met Lys Arg Thr Ser Gln Leu Lys Trp
            355                 360                 365

Ala Leu Gly Glu Asn Met Ala Pro Glu Lys Val Asp Phe Asp Asp Cys
        370                 375                 380

Lys Asp Val Gly Asp Leu Lys Gln Tyr Asp Ser Asp Glu Pro Glu Pro
385                 390                 395                 400

Arg Ser Leu Ala Ser Trp Val Gln Asn Glu Phe Asn Lys Ala Cys Glu
                405                 410                 415

Leu Thr Asp Ser Ser Trp Ile Glu Leu Asp Glu Ile Gly Glu Asp Val
                420                 425                 430

Ala Pro Ile Glu His Ile Ala Ser Met Arg Arg Asn Tyr Phe Thr Ala
            435                 440                 445

Glu Val Ser His Cys Arg Ala Thr Glu Tyr Ile Met Lys Gly Val Tyr
```

```
                450             455             460
Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
                500                 505                 510

Asn Asp Thr Asp Val Val Asn Phe Val Ser Met Glu Phe Ser Leu Thr
                515                 520                 525

Asp Pro Arg Leu Glu Pro His Lys Trp Glu Lys Tyr Cys Val Leu Glu
                530                 535                 540

Ile Gly Asp Met Leu Leu Arg Thr Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
                580                 585                 590

Glu Ser Met Ile Glu Ala Glu Ser Ser Val Lys Glu Lys Asp Met Thr
                595                 600                 605

Lys Glu Phe Phe Glu Asn Lys Ser Glu Thr Trp Pro Ile Gly Glu Ser
                610                 615                 620

Pro Arg Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
                660                 665                 670

Arg Asp Asn Leu Glu Pro Gly Thr Phe Asp Leu Gly Gly Leu Tyr Glu
                675                 680                 685

Ala Ile Glu Glu Cys Leu Ile Asn Asp Pro Trp Val Leu Leu Asn Ala
                690                 695                 700

Ser Trp Phe Asn Ser Phe Leu Thr His Ala Leu Lys
705                 710                 715

<210> SEQ ID NO 16
<211> LENGTH: 757
<212> TYPE: PRT
<213> ORGANISM: Unknown
<220> FEATURE:
<223> OTHER INFORMATION: Influenza

<400> SEQUENCE: 16

Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
                35                  40                  45

Tyr Ser Glu Lys Gly Lys Trp Thr Thr Asn Thr Glu Thr Gly Ala Pro
                50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
```

```
               100                 105                 110
Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
130             135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asn Lys
                165                 170                 175

Glu Glu Ile Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
            195                 200                 205

Lys Gln Arg Leu Asn Lys Arg Gly Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
            275                 280                 285

Met Met Thr Asn Ser Gln Asp Thr Glu Ile Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Ile
                325                 330                 335

Leu Ser Met Ala Pro Ile Met Phe Ser Asn Lys Met Ala Arg Leu Gly
            340                 345                 350

Lys Gly Tyr Met Phe Glu Ser Lys Arg Met Lys Ile Arg Thr Gln Ile
            355                 360                 365

Pro Ala Glu Met Leu Ala Ser Ile Asp Leu Lys Tyr Phe Asn Glu Ser
370                 375                 380

Thr Lys Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Ile Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
        450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Val Asn Glu Ser Ala Asp Met Ser Ile Gly Val Thr
            515                 520                 525
```

```
Val Ile Lys Asn Asn Met Ile Asn Asn Asp Leu Gly Pro Ala Thr Ala
            530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Lys Val Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Asp Tyr Arg Gly Arg Leu
            610                 615                 620

Cys Asn Pro Leu Asn Pro Phe Val Ser His Lys Glu Ile Asp Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Val Asp Phe Glu Ser Gly Arg Ile Lys
                725                 730                 735

Lys Glu Glu Phe Ser Glu Ile Met Lys Ile Cys Ser Thr Ile Glu Glu
            740                 745                 750

Leu Arg Arg Gln Lys
        755

<210> SEQ ID NO 17
<211> LENGTH: 759
<212> TYPE: PRT
<213> ORGANISM: Unknown
<220> FEATURE:
<223> OTHER INFORMATION: Influenza

<400> SEQUENCE: 17

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Arg Tyr Pro Ile Thr Ala Asp Lys Arg Ile Met
    50                  55                  60

Asp Met Ile Pro Glu Arg Asn Glu Gln Gly Gln Thr Leu Trp Ser Lys
65                  70                  75                  80

Thr Asn Asp Ala Gly Ser Asp Arg Val Met Val Ser Pro Leu Ala Val
                85                  90                  95

Thr Trp Trp Asn Arg Asn Gly Pro Thr Thr Ser Thr Val His Tyr Pro
            100                 105                 110

Lys Val Tyr Lys Thr Tyr Phe Glu Lys Val Glu Arg Leu Lys His Gly
        115                 120                 125
```

```
Thr Phe Gly Pro Val His Phe Arg Asn Gln Val Lys Ile Arg Arg Arg
        130                 135                 140
Val Asp Thr Asn Pro Gly His Ala Asp Leu Ser Ala Lys Glu Ala Gln
145                 150                 155                 160
Asp Val Ile Met Glu Val Val Phe Pro Asn Glu Val Gly Ala Arg Ile
                165                 170                 175
Leu Thr Ser Glu Ser Gln Leu Ala Ile Thr Lys Glu Lys Lys Glu Glu
                180                 185                 190
Leu Gln Asp Cys Lys Ile Ala Pro Leu Met Val Ala Tyr Met Leu Glu
            195                 200                 205
Arg Glu Leu Val Arg Lys Thr Arg Phe Leu Pro Val Ala Gly Gly Thr
210                 215                 220
Gly Ser Val Tyr Ile Glu Val Leu His Leu Thr Gln Gly Thr Cys Trp
225                 230                 235                 240
Glu Gln Met Tyr Thr Pro Gly Gly Glu Val Arg Asn Asp Asp Val Asp
                245                 250                 255
Gln Ser Leu Ile Ile Ala Ala Arg Asn Ile Val Arg Arg Ala Ala Val
                260                 265                 270
Ser Ala Asp Pro Leu Ala Ser Leu Leu Glu Met Cys His Ser Thr Gln
        275                 280                 285
Ile Gly Gly Val Arg Met Val Asp Ile Leu Arg Gln Asn Pro Thr Glu
        290                 295                 300
Glu Gln Ala Val Asp Ile Cys Lys Ala Ala Ile Gly Leu Arg Ile Ser
305                 310                 315                 320
Ser Ser Phe Ser Phe Gly Gly Phe Thr Phe Lys Arg Thr Ser Gly Ser
                325                 330                 335
Ser Val Lys Lys Glu Glu Glu Val Leu Thr Gly Asn Leu Gln Thr Leu
            340                 345                 350
Lys Ile Arg Val His Glu Gly Tyr Glu Glu Phe Thr Met Val Gly Arg
            355                 360                 365
Arg Ala Thr Ala Ile Leu Arg Lys Ala Thr Arg Arg Leu Ile Gln Leu
        370                 375                 380
Ile Val Ser Gly Arg Asp Glu Gln Ser Ile Ala Glu Ala Ile Ile Val
385                 390                 395                 400
Ala Met Val Phe Ser Gln Glu Asp Cys Met Ile Lys Ala Val Arg Gly
                405                 410                 415
Asp Leu Asn Phe Val Asn Arg Ala Asn Gln Arg Leu Asn Pro Met His
                420                 425                 430
Gln Leu Leu Arg His Phe Gln Lys Asp Ala Lys Val Leu Phe Gln Asn
            435                 440                 445
Trp Gly Ile Glu Ser Ile Asp Asn Val Met Gly Met Ile Gly Ile Leu
450                 455                 460
Pro Asp Met Thr Pro Ser Thr Glu Met Ser Leu Arg Gly Ile Arg Val
465                 470                 475                 480
Ser Lys Met Gly Val Asp Glu Tyr Ser Ser Thr Glu Arg Val Val Val
                485                 490                 495
Ser Ile Asp Arg Phe Leu Arg Val Arg Asp Gln Arg Gly Asn Val Leu
                500                 505                 510
Leu Ser Pro Glu Glu Val Ser Glu Thr Gln Gly Thr Glu Lys Leu Thr
        515                 520                 525
Ile Thr Tyr Ser Ser Ser Met Met Trp Glu Ile Asn Gly Pro Glu Ser
        530                 535                 540
```

Val Leu Val Asn Thr Tyr Gln Trp Ile Ile Arg Asn Trp Glu Ile Val
545                 550                 555                 560

Lys Ile Gln Trp Ser Gln Asp Pro Thr Met Leu Tyr Asn Lys Met Glu
            565                 570                 575

Phe Glu Pro Phe Gln Ser Leu Val Pro Lys Ala Thr Arg Ser Arg Tyr
            580                 585                 590

Ser Gly Phe Val Arg Thr Leu Phe Gln Gln Met Arg Asp Val Leu Gly
        595                 600                 605

Thr Phe Asp Thr Val Gln Ile Ile Lys Leu Leu Pro Phe Ala Ala Ala
    610                 615                 620

Pro Pro Glu Gln Ser Arg Met Gln Phe Ser Ser Leu Thr Val Asn Val
625                 630                 635                 640

Arg Gly Ser Gly Leu Arg Ile Leu Val Arg Gly Asn Ser Pro Val Phe
            645                 650                 655

Asn Tyr Asn Lys Ala Thr Lys Arg Leu Thr Val Leu Gly Lys Asp Ala
            660                 665                 670

Gly Ala Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Lys Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
            725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 18
<211> LENGTH: 319
<212> TYPE: PRT
<213> ORGANISM: Unknown
<220> FEATURE:
<223> OTHER INFORMATION: Influenza

<400> SEQUENCE: 18

Met Ala Ser Gln Gly Thr Lys Arg Ser Tyr Glu Gln Met Glu Thr Gly
1               5                   10                  15

Gly Glu Arg Gln Asp Ala Thr Glu Ile Arg Ala Ser Val Gly Arg Met
            20                  25                  30

Ile Gly Gly Ile Gly Arg Phe Tyr Ile Gln Met Cys Thr Glu Leu Lys
        35                  40                  45

Leu Ser Asp Tyr Asp Gly Arg Leu Ile Gln Asn Ser Ile Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
            85                  90                  95

Tyr Arg Arg Val Asp Gly Lys Trp Met Arg Glu Leu Ile Leu Tyr Asp
            100                 105                 110

Lys Glu Glu Ile Arg Arg Val Trp Arg Gln Ala Asn Asn Gly Glu Asp
        115                 120                 125

Ala Thr Ala Gly Leu Thr His Ile Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
            165                 170                 175

Gly Ala Ala Gly Ala Ala Val Lys Gly Val Gly Thr Ile Ala Met Glu
            180                 185                 190

Leu Ile Arg Met Ile Lys Arg Gly Ile Asn Asp Arg Asn Phe Trp Arg
            195                 200                 205

Gly Glu Asn Gly Arg Arg Thr Arg Val Ala Tyr Glu Arg Met Cys Asn
            210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
            245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
            275                 280                 285

His Asp Phe Glu Arg Glu Gly Tyr Ser Leu Val Gly Ile Asp Pro Phe
            290                 295                 300

Lys Leu Leu Gln Asn Ser Gln Val Val Ser Leu Met Arg Pro Asn
305                 310                 315

<210> SEQ ID NO 19
<211> LENGTH: 252
<212> TYPE: PRT
<213> ORGANISM: Unknown
<220> FEATURE:
<223> OTHER INFORMATION: Influenza

<400> SEQUENCE: 19

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Ser Val Phe
            20                  25                  30

Ala Gly Lys Asn Thr Asp Leu Glu Ala Leu Met Glu Trp Leu Lys Thr
            35                  40                  45

Arg Pro Ile Leu Ser Pro Leu Thr Lys Gly Ile Leu Gly Phe Val Phe
50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Arg Ala
            85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
            115                 120                 125

Gly Leu Ile Tyr Asn Arg Met Gly Thr Val Thr Thr Glu Ala Ala Phe
            130                 135                 140

Gly Leu Val Cys Ala Thr Cys Glu Gln Ile Ala Asp Ser Gln His Arg
145                 150                 155                 160

Ser His Arg Gln Met Ala Thr Thr Thr Asn Pro Leu Ile Arg His Glu
            165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Thr Arg Gln Met Val His Ala Met Arg Thr Ile Gly Thr His Pro Ser
    210                 215                 220

Ser Ser Ala Gly Leu Lys Asp Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 20
<211> LENGTH: 219
<212> TYPE: PRT
<213> ORGANISM: Unknown
<220> FEATURE:
<223> OTHER INFORMATION: Influenza

<400> SEQUENCE: 20

Met Asp Ser Asn Thr Met Ser Ser Phe Gln Val Asp Cys Phe Leu Trp
1               5                   10                  15

His Ile Arg Lys Arg Phe Ala Asp Asn Gly Leu Gly Asp Ala Pro Phe
                20                  25                  30

Leu Asp Arg Leu Arg Arg Asp Gln Lys Ser Leu Lys Gly Arg Gly Asn
            35                  40                  45

Thr Leu Gly Leu Asp Ile Glu Thr Ala Thr Leu Val Gly Lys Gln Ile
    50                  55                  60

Val Glu Trp Ile Leu Lys Glu Glu Ser Ser Glu Thr Leu Arg Met Thr
65                  70                  75                  80

Ile Ala Ser Val Pro Thr Ser Arg Tyr Leu Ser Asp Met Thr Leu Glu
                85                  90                  95

Glu Met Ser Arg Asp Trp Phe Met Leu Met Pro Arg Gln Lys Ile Ile
                100                 105                 110

Gly Pro Leu Cys Val Arg Leu Asp Gln Ala Ile Met Glu Lys Asn Ile
            115                 120                 125

Val Leu Lys Ala Asn Phe Ser Val Ile Phe Asn Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Tyr Glu Asp Val Lys Asn
                165                 170                 175

Ala Val Gly Val Leu Ile Gly Gly Leu Glu Trp Asn Gly Asn Thr Val
                180                 185                 190

Arg Val Ser Glu Asn Ile Gln Arg Phe Ala Trp Arg Asn Cys Asp Glu
            195                 200                 205

Asn Gly Arg Pro Ser Leu Pro Pro Glu Gln Lys
    210                 215

<210> SEQ ID NO 21
<211> LENGTH: 2151
<212> TYPE: DNA
<213> ORGANISM: Unknown
<220> FEATURE:
<223> OTHER INFORMATION: Influenza

<400> SEQUENCE: 21
atggaagact tgtgcgaca atgcttcaat ccaatgatcg tcgagcttgc ggaaaaggca        60
atgaaagaat atgggaaga tccgaaaatc gaaactaaca agtttgctgc aatatgcaca       120
catttggaag tttgtttcat gtattcggat ttccatttca tcgacgaacg ggtgaatca       180

```
ataattgtag aatctggtga cccgaatgca ctattgaagc accgatttga gataattgaa    240
ggaagagacc gaatcatggc ctggacagtg gtgaacagta tatgtaacac aacagggta     300 gagaagccta aatttcttcc tgatttgtat gattacaaag agaaccggtt cattgaaatt    360
ggagtaacac ggagggaagt ccacatatat tacctagaga aagccaacaa aataaaatct    420
gagaagacac acattcacat cttttcattc actggagagg agatggccac caaagcggac    480
tacacccttg acgaagagag cagggcaaga atcaaaacta ggcttttcac tataagacaa    540
gaaatggcca gtaggagtct atgggattcc tttcgtcagt ccgaaagagg cgaagagaca    600
attgaagaaa aatttgagat tacaggaact atgcgcaagc ttgccgacca aagtctccca    660
ccgaacttcc ccagccttga aaactttaga gcctatgtag atggattcga gccgaacggc    720
tgcattgagg gcaagctttc ccaaatgtca aaagaagtga acgccaaaat tgaaccattc    780
ttgaggacga caccacgccc cctcagattg cctgatgggc tctttgcca  tcagcggtca    840 aagttcctgc tgatggatgc tctgaaatta agtattgaag acccgagtca cgaggggag    900 ggaataccac tatatgatgc aatcaaatgc atgaagacat tctttggctg gaaagagcct    960
aacatagtca aaccacatga gaaaggcata aatcccaatt acctcatggc ttggaagcag   1020
gtgctagcag agctacagga cattgaaaat gaagagaaga tcccaaggac aaagaacatg   1080
aagagaacaa gccaattgaa gtgggcactc ggtgaaaata tggcaccaga aaaagtagac   1140
tttgatgact gcaaagatgt tggagacctt aaacagtatg acagtgatga gccagagccc   1200
agatctctag caagctgggt ccaaaatgaa ttcaataagg catgtgaatt gactgattca   1260
agctggatag aacttgatga aataggagaa gatgttgccc cgattgaaca tatcgcaagc   1320
atgaggagga actatttac  agcagaagtg tccccactgca gggctactga atacataatg   1380
aagggagtgt acataaatac ggccttgctc aatgcatcct gtgcagccat ggatgacttt   1440
cagctgatcc caatgataag caatgtagg accaaagaag gaagacggaa aacaaacctg   1500
tatgggttca ttataaaagg aaggtctcat ttgagaaatg atactgatgt ggtgaacttt   1560
gtaagtatgg agttctcact cactgacccg agactggagc cacacaaatg ggaaaaatac   1620
tgtgttcttg aaataggaga catgctcttg aggactgcga taggccaagt gtcgaggccc   1680
atgttcctat atgtgagaac caatggaacc tccaagatca agatgaaatg gggcatggaa   1740
atgaggcgct gccttcttca gtctcttcag cagattgaga gcatgattga ggccgagtct   1800
tctgtcaaag agaaagacat gaccaaggaa ttctttgaaa acaaatcgga aacatggcca   1860
atcggagagt cacccaggg  agtggaggaa ggctctattg ggaaagtgtg caggaccttc   1920
ctggcaaaat ctgtattcaa cagtctatat gcgtctccac aacttgaggg gttttcggct   1980
gaatctagaa aattgcttct cattgttcag gcacttaggg acaacctgga acctggaacc   2040
ttcgatcttg ggggctata  tgaagcaatc gaggagtgcc tgattaatga tcctgggtt    2100 ttgcttaatg catcttggtt caactccttc ctcacacatg cactgaagta g             2151
```

<210> SEQ ID NO 22
<211> LENGTH: 2341
<212> TYPE: DNA
<213> ORGANISM: Unknown
<220> FEATURE:
<223> OTHER INFORMATION: Influenza

<400> SEQUENCE: 22

```
agcgaaagca ggcaaaccat ttgaatggat gtcaatccga ctctactttt cctaaaaatt    60
```

```
ccagcgcaaa atgccataag caccacattc ccttatactg gagatcctcc atacagccat      120
ggaacaggaa caggatacac catggacaca gtaaacagaa cacaccaata ctcagaaaag      180
ggaaagtgga cgacaaacac agagactggt gcaccccagc tcaacccgat tgatggacca      240
ctacctgagg ataatgaacc aagtgggtat gcacaaacag actgtgttct agaggctatg      300
gctttccttg aagaatccca cccaggaata tttgagaatt catgccttga acaatggaa       360
gttgttcaac aaacaagggt agataaacta actcaaggtc gccagactta tgattggaca      420
ttaaacagaa atcaaccggc agcaactgca ttggccaaca ccatagaagt ctttagatcg      480
aatggcctaa cagctaatga gtcaggaagg ctaatagatt tcttaaagga tgtaatggaa      540
tcaatgaaca agaggaaat agagataaca acccactttc aaagaaaaag gagagtaaga        600
gacaacatga ccaagaagat ggtcacgcaa agaacaatag gaagaaaaa acaaagactg        660
aataagagag gctatctaat aagagcactg acattaaata cgatgaccaa agatgcagag      720
agaggcaagt taaaagaag ggctatcgca acacctggga tgcagattag aggtttcgta       780
tactttgttg aaactttagc taggagcatt tgcgaaaagc ttgaacagtc tgggctccca      840
gtaggggca atgaaaagaa ggccaaactg gcaaatgttg tgagaaagat gatgactaat       900
tcacaagaca cagagatttc tttcacaatc actgggggaca cactaagtg gaatgaaaat       960
caaaatcctc gaatgttcct ggcgatgatt acatatatca ccagaaatca acccgagtgg      1020
ttcagaaaca tcctgagcat ggcacccata atgttctcaa acaaaatggc aagactaggg      1080
aaagggtaca tgttcgagag taaaagaatg aagattcgaa cacaaatacc agcagaaatg      1140
ctagcaagca ttgacctgaa gtacttcaat gaatcaacaa agaagaaaat tgagaaaata      1200
aggcctcttc taatagatgg cacagcatca ctgagtcctg ggatgatgat gggcatgttc      1260
aacatgctaa gtacggtctt gggagtctcg atactgaatc ttggacaaaa gaaatacacc      1320
aagacaatat actggtggga tgggctccaa tcatccgacg attttgctct catagtgaat      1380
gcaccaaacc atgagggaat acaagcagga gtggacagat ctacaggac ctgcaagtta       1440
gtgggaatca acatgagcaa aaagaagtcc tatataaata agacagggac atttgaattc      1500
acaagctttt tttatcgcta tggatttgtg gctaatttta gcatggagct acccagctt       1560
ggagtgtctg gagtaaatga atcagctgac atgagtattg gagtaacagt gataaagaac      1620
aacatgataa acaatgacct tggacctgca acggcccaga tggctcttca attgttcatc      1680
aaagactaca gatacacata taggtgccat aggggagaca cacaaattca gacaagaaga      1740
tcatttgagt taaagaagct gtgggatcaa acccaatcaa aggtagggct attagtatca      1800
gatggaggac caaacttata caatatacgg aatcttcaca ttcctgaagt ctgcttaaaa      1860
tgggagctaa tggatgatga ttatcgggga agactttgta atcccctgaa tccctttgtc      1920
agtcataaag agattgattc tgtaaacaat gctgtggtaa tgccagccca tggtccagcc      1980
aaaagcatgg aatatgatgc cgttgcaact cacacattcct ggattcccaa gaggaatcgt      2040
tctattctca acacaagcca agggaatt cttgaggatg aacagatgta ccagaagtgc        2100
tgcaatctat tcgagaaatt tttccctagc agttcatata ggagaccggt tggaatttct      2160
agcatggtgg aggccatggt gtctagggcc cggattgatg ccagggtcga cttcgagtct      2220
ggacggatca agaaagaaga gttctctgag atcatgaaga tctgttccac cattgaagaa      2280
ctcagacggc aaaaataatg aatttaactt gtccttcatg aaaaaatgcc ttgtttctac      2340
t                                                                     2341
```

```
<210> SEQ ID NO 23
<211> LENGTH: 2280
<212> TYPE: DNA
<213> ORGANISM: Unknown
<220> FEATURE:
<223> OTHER INFORMATION: Influenza

<400> SEQUENCE: 23
atggagagaa taaaagaact gagagatcta atgtcgcagt cccgcactcg cgagatactc      60
actaagacca ctgtggacca tatggccata atcaaaaagt acacatcagg aaggcaagag     120
aagaaccccg cactcagaat gaagtggatg atggcaatga gatacccaat tacagcagac     180
aagagaataa tggacatgat tccagagagg aatgaacaag acaaaccct ctggagcaaa      240 acaaacgatg ctggatcaga ccgagtgatg gtatcacctc tggccgtaac atggtggaat     300
aggaatggcc caacaacaag tacagttcat taccctaagg tatataaaac ttatttcgaa     360
aaggtcgaaa ggttgaaaca tggtaccttc ggccctgtcc acttcagaaa tcaagttaaa     420
ataaggagga gagttgatac aaaccctggc catgcagatc tcagtgccaa ggaggcacag     480
gatgtgatta tggaagttgt tttcccaaat gaagtggggg caagaatact gacatcagag     540
tcacagctgg caataacaaa agagaagaaa gaagagctcc aggattgtaa aattgctccc     600
ttgatggtgg cgtacatgct agaaagagaa ttggtccgta aaacaaggtt tctcccagta     660
gccggcggaa caggcagtgt ttatattgaa gtgttgcact taacccaagg acgtgctgg     720 gagcagatgt acactccagg aggagaagtg agaaatgatg atgttgacca agtttgatt      780 atcgctgcta gaaacatagt aagaagagca gcagtgtcag cagacccatt agcatctctc     840
ttggaaatgt gccacagcac acagattgga ggagtaagga tggtggacat ccttagacag     900
aatccaactg aggaacaagc cgtagacata tgcaaggcag caatagggt gaggattagc      960 tcatctttca gttttggtgg gttcactttc aaaaggacaa gcggatcatc agtcaagaaa    1020
gaagaagaag tgctaacggg caaccctcca acactgaaaa taagagtaca tgaagggtat    1080
gaagaattca caatggttgg gagaagagca acagctattc tcagaaaggc aaccaggaga    1140
ttgatccagt tgatagtaag cgggagagac gagcagtcaa ttgctgaggc aataattgtg    1200
gccatggtat tctcacagga ggattgcatg atcaaggcag ttaggggcga tctgaactt     1260 gtcaataggg caaccagcg actgaacccc atgcaccaac tcttgaggca tttccaaaaa    1320
gatgcaaaag tgcttttcca gaactgggga attgaatcca tcgacaatgt gatgggaatg    1380
atcggaatac tgcccgacat gacccccaagc acggagatgt cgctgagagg ataagagtc    1440 agcaaaatgg gagtagatga atactccagc acggagagag tggtagtgag tattgaccga    1500
tttttaaggg ttagagatca aagagggaac gtactattgt ctcccgaaga agtcagtgaa    1560
acgcaaggaa ctgagaagtt gacaataact tattcgtcat caatgatgtg ggagatcaat    1620
ggccctgagt cagtgctagt caacacttat caatggataa tcaggaactg gaaaattgtg    1680
aaaattcaat ggtcacaaga tcccacaatg ttatacaaca aaatgaatt tgaaccattt    1740 cagtctcttg tccctaaggc aaccagaagc cggtacagtg gattcgtaag gacactgttc    1800
cagcaaatgc gggatgtgct tgggacattt gacactgtcc aaataataa acttctcccc    1860 tttgctgctg cccaccagag acagagtagg atgcaatttt cctcattgac tgtgaatgtg    1920
agaggatcag ggttgaggat actggtaaga ggcaattctc cagtattcaa ttacaacaag    1980
gcaaccaaac gacttacagt tcttggaaag gatgcaggtg cattgactga agatccagat    2040
gaaggcacat ctggggtgga gtctgctgtc ctgagaggat ttctcattt gggcaaagaa    2100
```

| gacaagagat atggcccagc attaagcatc aatgaactga gcaatcttgc aaaaggagag | 2160 |
| aaggctaatg tgctaattgg gcaaggggac gtagtgttgg taatgaaacg aaaacgggac | 2220 |
| tctagcatac ttactgacag ccagacagcg accaaaagaa ttcggatggc catcaattag | 2280 |

<210> SEQ ID NO 24
<211> LENGTH: 958
<212> TYPE: DNA
<213> ORGANISM: Unknown
<220> FEATURE:
<223> OTHER INFORMATION: Influenza

<400> SEQUENCE: 24

| atggcgtctc aaggcaccaa acgatcatat gaacaaatgg agactggtgg ggagcgccag | 60 |
| gatgccacag aaatcagagc atctgtcgga agaatgattg gtggaatcgg gagattctac | 120 |
| atccaaatgt gcactgaact caaactcagt gattatgatg acgactaat ccagaatagc | 180 |
| ataacaatag agaggatggt gctttctgct tttgatgaga aagaaataa atacctagaa | 240 |
| gagcatccca gtgctgggaa ggaccctaag aaaacaggag acccatata tagaagagta | 300 |
| gacggaaagt ggatgagaga actcatcctt tatgacaaag aagaaataag gagagtttgg | 360 |
| cgccaagcaa acaatggcga agatgcaaca gcaggtctta ctcatatcat gatttggcat | 420 |
| tccaacctga tgatgccac atatcagaga acaagagcgc ttgttcgcac cggaatggat | 480 |
| cccagaatgt gctctctaat gcaaggttca acacttccca aaggtctgg tgccgcaggt | 540 |
| gctgcggtga aggagttgg aacaatagca atggagttaa tcagaatgat caaacgtgga | 600 |
| atcaatgacc gaaatttctg gagggtgaa atggacgaa ggacaagggt tgcttatgaa | 660 |
| agaatgtgca atatcctcaa aggaaaattt caaacagctg cccagagggc aatgatggat | 720 |
| caagtaagag aaagtcgaaa cccaggaaac gctgagattg aagacctcat tttcctggca | 780 |
| cggtcagcac tcattctgag gggatcagtt gcacataaat cctgcctgcc tgcttgtgtg | 840 |
| tatgggcttg cagtagcaag tgggcatgac tttgaaaggg aagggtactc actggtcggg | 900 |
| atagacccat tcaaattact ccaaaacagc caagtggtca gcctgatgag accaaatg | 958 |

<210> SEQ ID NO 25
<211> LENGTH: 982
<212> TYPE: DNA
<213> ORGANISM: Unknown
<220> FEATURE:
<223> OTHER INFORMATION: Influenza

<400> SEQUENCE: 25

| atgagtcttc taaccgaggt cgaaacgtac gttctttcta tcatcccgtc aggccccctc | 60 |
| aaagccgaga tcgcgcagag actggaaagt gtctttgcag aaagaacac agatcttgag | 120 |
| gctctcatgg aatggctaaa gacaagacca atcttgtcac ctctgactaa gggaatttta | 180 |
| ggatttgtgt tcacgctcac cgtgcccagt gagcgaggac tgcagcgtag acgctttgtc | 240 |
| caaaatgccc taatgggaa tgggacccg aacaacatgg atagagcagt taaactatac | 300 |
| aagaagctca aaagagaaat aacgttccat ggggccaagg aggtgtcact aagctattca | 360 |
| actggtgcac ttgccagttg catgggcctc atatacaaca ggatgggaac agtgaccaca | 420 |
| gaagctgctt ttggtctagt gtgtgccact tgtgaacaga ttgctgattc acagcatcgg | 480 |
| tctcacagac agatggctac taccaccaat ccactaatca ggcatgaaaa cagaatggtg | 540 |
| ctggctagca ctacggcaaa ggctatgaa cagatggctg atcgagtga acaggcagcg | 600 |
| gaggccatgg aggttgctaa tcagactagg cagatggtac atgcaatgag aactattggg | 660 |

```
actcatccta gctccagtgc tggtctgaaa gatgaccttc ttgaaaattt gcaggcctac    720
cagaagcgaa tgggagtgca gatgcagcga ttcaagtgat cctctcgtca ttgcagcaaa    780
tatcattggg atcttgcacc tgatattgtg gattactgat cgtctttttt tcaaatgtat    840
ttatcgtcgc tttaaatacg gtttgaaaag agggccttct acggaaggag tgcctgagtc    900
catgagggaa gaatatcaac aggaacagca gagtgctgtg gatgttgacg atggtcattt    960
tgtcaacata gagctagagt aa                                             982
```

<210> SEQ ID NO 26
<211> LENGTH: 865
<212> TYPE: DNA
<213> ORGANISM: Unknown
<220> FEATURE:
<223> OTHER INFORMATION: Influenza

<400> SEQUENCE: 26

```
atggactcca acaccatgtc aagctttcag gtagactgtt tcctttggca atccgcaag     60 cgatttgcag acaatggatt gggtgatgcc ccattccttg atcggctccg ccgagatcaa    120
aagtccttaa aggaagagg caacacccctt ggcctcgata tcgaaacagc cactcttgtt    180
gggaaacaaa tcgtggaatg gatcttgaaa gaggaatcca gcgagacact agaatgaca    240 attgcatctg tacctacttc gcgctacctt tctgacatga ccctcgagga aatgtcacga    300
gactggttca tgctcatgcc taggcaaaag ataataggcc ctctttgcgt gcgattggac    360
caggcgatca tggaaaagaa catagtactg aaagcgaact tcagtgtaat ctttaaccga    420
ttagagacct tgatactact aagggctttc actgaggagg gagcaatagt tggagaaatt    480
tcaccattac cttctcttcc aggacatact tatgaggatg tcaaaaatgc agttggggtc    540
ctcatcggag acttgaatg gaatggtaac acggttcgag tctctgaaaa atacagaga    600 ttcgcttgga gaaactgtga tgagaatggg agaccttcac tacctccaga gcagaaatga    660
aaagtggcga gagcaattgg gacagaaatt tgaggaaata aggtggttaa ttgaagaaat    720
gcggcacaga ttgaaagcga cagagaatag tttcgaacaa ataacattta tgcaagccctt    780 acaactactg cttgaagtag aacaagagat aagagctttc tcgtttcagc ttatttaatg    840
ataaaaaaca cccttgtttc tactg                                          865
```

<210> SEQ ID NO 27
<211> LENGTH: 758
<212> TYPE: PRT
<213> ORGANISM: Unknown
<220> FEATURE:
<223> OTHER INFORMATION: Influenza

<400> SEQUENCE: 27

```
Met Asp Val Asn Pro Thr Leu Leu Phe Leu Lys Ile Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
```

```
                     85                  90                  95
Glu Ser His Pro Gly Ile Phe Glu Asn Ser Cys Leu Glu Thr Met Glu
                100                 105                 110

Val Val Gln Gln Thr Arg Val Asp Arg Leu Thr Gln Gly Arg Gln Thr
                115                 120                 125

Tyr Asp Trp Thr Leu Asn Arg Asn Gln Pro Ala Ala Thr Ala Leu Ala
            130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Ile Glu Ile Thr Thr His Phe Gln Arg Lys Arg Arg Val Arg
                180                 185                 190

Asp Asn Met Thr Lys Lys Met Val Thr Gln Arg Thr Ile Gly Lys Lys
                195                 200                 205

Lys Gln Arg Val Asn Lys Arg Ser Tyr Leu Ile Arg Ala Leu Thr Leu
                210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
                275                 280                 285

Met Met Thr Asn Ser Gln Asp Thr Glu Leu Ser Phe Thr Ile Thr Gly
                290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Arg Met Lys Leu Arg Thr Gln Ile
                355                 360                 365

Pro Ala Glu Met Leu Ala Ser Ile Asp Leu Lys Tyr Phe Asn Glu Ser
                370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Gly Met Phe Asn Met Leu Ser
                405                 410                 415

Thr Val Leu Gly Val Ser Ile Leu Asn Leu Gly Gln Lys Lys Tyr Thr
                420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Ile Gln Ala Gly Val Asp
                450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510
```

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asp Tyr Gln Gly Arg Leu
                610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
                675                 680                 685

Tyr Gln Lys Cys Cys Asn Leu Phe Glu Lys Phe Phe Pro Ser Ser Ser
                690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
                740                 745                 750

Leu Arg Arg Gln Lys Gln
        755

<210> SEQ ID NO 28
<211> LENGTH: 716
<212> TYPE: PRT
<213> ORGANISM: Unknown
<220> FEATURE:
<223> OTHER INFORMATION: Influenza

<400> SEQUENCE: 28

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Ile Val Glu
        50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
                100                 105                 110

```
Lys Glu Asn Arg Phe Ile Glu Ile Gly Val Thr Arg Arg Glu Val His
            115                 120                 125
Ile Tyr Tyr Leu Glu Lys Ala Asn Lys Ile Lys Ser Glu Lys Thr His
        130                 135                 140
Ile His Ile Phe Ser Phe Thr Gly Glu Met Ala Thr Lys Ala Asp
145                 150                 155                 160
Tyr Thr Leu Asp Glu Glu Ser Arg Ala Arg Ile Lys Thr Arg Leu Phe
                165                 170                 175
Thr Ile Arg Gln Glu Met Ala Ser Arg Gly Leu Trp Asp Ser Phe Arg
            180                 185                 190
Gln Ser Glu Arg Gly Glu Thr Ile Glu Glu Arg Phe Glu Ile Thr
        195                 200                 205
Gly Thr Met Arg Lys Leu Ala Asp Gln Ser Leu Pro Pro Asn Phe Ser
    210                 215                 220
Ser Leu Glu Asn Phe Arg Ala Tyr Val Asp Gly Phe Glu Pro Asn Gly
225                 230                 235                 240
Tyr Ile Glu Gly Lys Leu Ser Gln Met Ser Lys Glu Val Asn Ala Arg
                245                 250                 255
Ile Glu Pro Phe Leu Lys Thr Thr Pro Arg Pro Leu Arg Leu Pro Asn
            260                 265                 270
Gly Pro Pro Cys Ser Gln Arg Ser Lys Phe Leu Leu Met Asp Ala Leu
    275                 280                 285
Lys Leu Ser Ile Glu Asp Pro Ser His Glu Gly Gly Ile Pro Leu
290                 295                 300
Tyr Asp Ala Ile Lys Cys Met Arg Thr Phe Phe Gly Trp Lys Glu Pro
305                 310                 315                 320
Asn Val Val Lys Pro His Glu Lys Gly Ile Asn Pro Asn Tyr Leu Leu
                325                 330                 335
Ser Trp Lys Gln Val Leu Ala Glu Leu Gln Asp Ile Glu Asn Glu Glu
            340                 345                 350
Lys Ile Pro Lys Thr Lys Asn Met Lys Lys Thr Ser Gln Leu Lys Trp
        355                 360                 365
Ala Leu Gly Glu Asn Met Ala Pro Glu Lys Val Asp Phe Asp Asp Cys
    370                 375                 380
Lys Asp Val Gly Asp Leu Lys Gln Tyr Asp Ser Asp Glu Pro Glu Leu
385                 390                 395                 400
Arg Ser Leu Ala Ser Trp Ile Gln Asn Glu Phe Asn Lys Ala Cys Glu
                405                 410                 415
Leu Thr Asp Ser Ser Trp Ile Glu Leu Asp Glu Ile Gly Glu Asp Val
            420                 425                 430
Ala Pro Ile Glu His Ile Ala Ser Met Arg Arg Asn Tyr Phe Thr Ser
        435                 440                 445
Glu Val Ser His Cys Arg Ala Thr Glu Tyr Ile Met Lys Gly Val Tyr
    450                 455                 460
Ile Asn Thr Ala Leu Leu Asn Ala Ser Cys Ala Ala Met Asp Asp Phe
465                 470                 475                 480
Gln Leu Ile Pro Met Ile Ser Lys Cys Arg Thr Lys Glu Gly Arg Arg
                485                 490                 495
Lys Thr Asn Leu Tyr Gly Phe Ile Ile Lys Gly Arg Ser His Leu Arg
            500                 505                 510
Asn Asp Thr Asp Val Val Asn Phe Val Ser Met Glu Phe Ser Leu Thr
        515                 520                 525
```

Asp Pro Arg Leu Glu Pro His Lys Trp Glu Lys Tyr Cys Val Leu Glu
    530                 535                 540

Ile Gly Asp Met Leu Ile Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
    675                 680                 685

Ala Ile Glu Glu Cys Leu Ile Asn Asp Pro Trp Val Leu Leu Asn Ala
690                 695                 700

Ser Trp Phe Asn Ser Phe Leu Thr His Ala Leu Ser
705                 710                 715

<210> SEQ ID NO 29
<211> LENGTH: 326
<212> TYPE: PRT
<213> ORGANISM: Unknown
<220> FEATURE:
<223> OTHER INFORMATION: Influenza

<400> SEQUENCE: 29

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

```
Gly Ala Ala Gly Ala Ala Val Lys Gly Val Gly Thr Met Val Met Glu
                180                 185                 190
Leu Val Arg Met Ile Lys Arg Gly Ile Asn Asp Arg Asn Phe Trp Arg
                195                 200                 205
Gly Glu Asn Gly Arg Lys Thr Arg Ile Ala Tyr Glu Arg Met Cys Asn
                210                 215                 220
Ile Leu Lys Gly Lys Phe Gln Thr Ala Ala Gln Lys Ala Met Met Asp
225                 230                 235                 240
Gln Val Arg Glu Ser Arg Asp Pro Gly Asn Ala Glu Phe Glu Asp Leu
                245                 250                 255
Thr Phe Leu Ala Arg Ser Ala Leu Ile Leu Arg Gly Ser Val Ala His
                260                 265                 270
Lys Ser Cys Leu Pro Ala Cys Val Tyr Gly Pro Ala Val Ala Ser Gly
                275                 280                 285
Tyr Asp Phe Glu Arg Glu Gly Tyr Ser Leu Val Gly Ile Asp Pro Phe
                290                 295                 300
Arg Leu Leu Gln Asn Ser Gln Val Tyr Ser Leu Ile Arg Pro Asn Glu
305                 310                 315                 320
Asn Pro Ala His Lys Ser
                325

<210> SEQ ID NO 30
<211> LENGTH: 252
<212> TYPE: PRT
<213> ORGANISM: Unknown
<220> FEATURE:
<223> OTHER INFORMATION: Influenza

<400> SEQUENCE: 30

Met Ser Leu Leu Thr Glu Val Glu Thr Tyr Val Leu Ser Ile Ile Pro
1               5                   10                  15
Ser Gly Pro Leu Lys Ala Glu Ile Ala Gln Arg Leu Glu Asp Val Phe
                20                  25                  30
Ala Gly Lys Asn Thr Asp Leu Glu Val Leu Met Glu Trp Leu Lys Thr
                35                  40                  45
Arg Pro Ile Leu Ser Pro Leu Thr Lys Gly Ile Leu Gly Phe Val Phe
                50                  55                  60
Thr Leu Thr Val Pro Ser Glu Arg Gly Leu Gln Arg Arg Arg Phe Val
65                  70                  75                  80
Gln Asn Ala Leu Asn Gly Asn Gly Asp Pro Asn Asn Met Asp Lys Ala
                85                  90                  95
Val Lys Leu Tyr Arg Lys Leu Lys Arg Glu Ile Thr Phe His Gly Ala
                100                 105                 110
Lys Glu Ile Ser Leu Ser Tyr Ser Ala Gly Ala Leu Ala Ser Cys Met
                115                 120                 125
Gly Leu Ile Tyr Asn Arg Met Gly Ala Val Thr Thr Glu Val Ala Phe
                130                 135                 140
Gly Leu Val Cys Ala Thr Cys Glu Gln Ile Ala Asp Ser Gln His Arg
145                 150                 155                 160
Ser His Arg Gln Met Val Thr Thr Thr Asn Pro Leu Ile Arg His Glu
                165                 170                 175
Asn Arg Met Val Leu Ala Ser Thr Thr Ala Lys Ala Met Glu Gln Met
                180                 185                 190
Ala Gly Ser Ser Glu Gln Ala Ala Glu Ala Met Glu Val Ala Ser Gln
                195                 200                 205
```

```
Ala Arg Gln Met Val Gln Ala Met Arg Thr Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 31
<211> LENGTH: 2299
<212> TYPE: DNA
<213> ORGANISM: Unknown
<220> FEATURE:
<223> OTHER INFORMATION: Influenza

<400> SEQUENCE: 31
aatatggaaa gaataaaaga gctaaggaat ctgatgtcac aatctcgcac tcgcgagata      60
cttacaaaaa ctactgtaga ccacatggcc ataatcaaga aatacacatc aggaagacag     120
gagaaaaacc catcacttag aatgaaatgg atgatggcaa tgaaataccc aattacagca     180
gataaaagga taacggaaat gattcctgaa agaaatgagc aaggacagac attatggagt     240
aaagtgaatg atgccggatc agaccgagtg atgatatcac ccctggctgt gacatggtgg     300
aacagaaatg gaccagtggc aagtactatt cactatccaa aaatctacaa aacttacttt     360
gaaaaggttg aaaggttaaa acatggaacc tttggccctg tacactttag aaaccaagtc     420
aaaatacgcc gaagagtcga cataaatcct ggtcatgcag acctcagcgc caaggaggca     480
caggatgtaa ttatggaagt tgtttttccct aatgaagtgg gagccagaat actaacatca     540
gaatcgcaat taacgataac caaggagaaa aagaagaac tccagaattg caaaatttcc     600
cctttgatgg ttgcatacat gttagagagg gaacttgtcc gcaaaacgag atttctcccg     660
gttgctggtg gaacaagcag tgtgtacatt gaagttttgc atttaacaca ggggacatgc     720
tgggagcaga tgtacactcc aggtggggag gtgaggaatg atgatgttga tcaaagccta     780
attattgctg ctaggaacat agtgagaaga gctgcagtat cagcagatcc actagcatct     840
ttattagaaa tgtgccatag cacacagatt ggtgggacaa ggatggtgga tattctcagg     900
caaaatccaa cagaagaaca agctgtggat atatgcaaag cagcaatggg gctgagaatc     960
agttcatcct tcagttttgg cggattcaca tttaagagaa caagtggatc atcagtcaaa    1020
agggaggaag aagtgctcac gggcaatctg caaacattga gctaactgt gcatgaggga    1080 tatgaagagt tcacaatggt tgggaaaagg caacagcta tactcagaaa agcaaccagg    1140
agattgattc aactaatagt gagtggaaga acgaacagt caatagtcga agcaatagtt    1200
gtagcaatgg tattctcaca agaagattgc atggtaaaag cagttagagg tgatctgaat    1260
ttcgttaata gagcgaatca gcggttgaat cccatgcatc aacttttgag acattttcag    1320
aaggatgcta aagtactttt cttaaattgg ggaattgaac ctatcgacaa tgtgatggga    1380
atgattggga tattacctga tatgactcca gtaccgaga tgtcaatgag gagagtgaga    1440
gtcagcaaaa tgggtgtaga tgaatactcc aatgctgaaa gggtagtggt gagcattgac    1500
cgttttttga gagtccggga ccaaagagga aatgtactac tgtctccaga ggaagtcagt    1560
gaaacacagg gaacagagaa actgacaata acttactctt catcaatgat gtgggagatt    1620
aatggccctg agtcagtgtt gatcaatacc tatcagtgga tcatcagaaa ctgggagact    1680
gttaaaattc agtggtctca gaaccctaca atgctataca ataaaatgga attcgagcca    1740
tttcagtctc tagtccctaa ggccattaga ggccaataca gtgggtttgt tagaactcta    1800
```

| | |
|---|---:|
| tttcaacaaa tgagggatgt gcttgggacc tttgacacaa ctcagataat aaaacttctt | 1860 |
| ccctttgcag ccgctccacc aaagcaaagt agaatgcaat tctcatcatt gactgtgaat | 1920 |
| gtgaggggat caggaatgag aatacttgta aggggtaatt ctccagtatt caactacaac | 1980 |
| aagaccacta agagactcac agtcctcgga aaggatgctg gcactttaac tgaagaccca | 2040 |
| gatgaaggca cagctggagt ggaatctgct gttctaaggg gattcctcat tctaggcaaa | 2100 |
| gaagatagaa gatatgggcc agcattaagc atcaatgaat tgagcaacct tgcgaagggg | 2160 |
| gaaaaagcta atgtgctaat tgggcaaggg gacgtagtgt tggtaatgaa acgaaaacgg | 2220 |
| gactctagca tacttactga cagccagaca gcgaccaaaa gaattcggat ggccatcaat | 2280 |
| taatttcgaa taatttaaa | 2299 |

<210> SEQ ID NO 32
<211> LENGTH: 2277
<212> TYPE: DNA
<213> ORGANISM: Unknown
<220> FEATURE:
<223> OTHER INFORMATION: Influenza

<400> SEQUENCE: 32

| | |
|---|---:|
| atggaacgca ttaaagaact gcgcaacctg atgagccaga gccgcacccg cgaaattctg | 60 |
| accaaaacca ccgtggatca tatggcgatt attaaaaaat ataccagcgg ccgccaggaa | 120 |
| aaaaacccga gcctgcgcat gaaatggatg atggcgatga aatatccgat taccgcggat | 180 |
| aaacgcatta ccgaaatgat tccggaacgc aacgaacagg ccagaccct gtggagcaaa | 240 |
| gtgaacgatg cgggcagcga tcgcgtgatg attagcccgc tggcggtgac ctggtggaac | 300 |
| cgcaacggcc cggtggcgag caccattcat tatccgaaaa tttataaaac ctattttgaa | 360 |
| aaagtggaac gcctgaaaca tggcaccttt ggcccggtgc attttcgcaa ccaggtgaaa | 420 |
| attcgccgcc gcgtggatat taacccgggc catgcggatc tgagcgcgaa agaagcgcag | 480 |
| gatgtgatta tggaagtggt gtttccgaac gaagtgggcg cgcgcattct gaccagcgaa | 540 |
| agccagctga ccattaccaa agaaaaaaaa gaagaactgc agaactgcaa aattagcccg | 600 |
| ctgatggtgg cgtatatgct ggaacgcgaa ctggtgcgca aaacccgctt tctgccggtg | 660 |
| gcgggcggca ccagcagcgt gtatattgaa gtgctgcatc tgacccaggg cacctgctgg | 720 |
| gaacagatgt ataccccggg cggcgaagtg cgcaacgatg atgtggatca gagcctgatt | 780 |
| attgcggcgc gcaacattgt gcgccgcgcg gcggtgagcg cggatccgct ggcgagcctg | 840 |
| ctggaaatgt gccatagcac ccagattggc ggcacccgca tggtggatat tctgcgccag | 900 |
| aacccgaccg aagaacaggc ggtggatatt tgcaaagcgg cgatgggcct gcgcattagc | 960 |
| agcagcttta gctttggcgg ctttacccttt aaacgcacca gcggcagcag cgtgaaacgc | 1020 |
| gaagaagaag tgctgaccgg caacctgcag accctgaaaa tgaccgtgca tgaaggctat | 1080 |
| gaagaattta ccatggtggg caaacgcgcg accgcgattc tgcgcaaagc gacccgccgc | 1140 |
| ctgattcagc tgattgtgag cggccgcgat gaacagagca ttgtggaagc gattgtggtg | 1200 |
| gcgatggtgt ttagccagga agattgcatg gtgaaagcgg tgcgcggcga tctgaacttt | 1260 |
| gtgaaccgcg cgaaccagcg cctgaacccg atgcatcagc tgctgcgcca ttttcagaaa | 1320 |
| gatgcgaaag tgctgtttct gaactgggc attgaaccga ttgataacgt gatgggcatg | 1380 |
| attggcattc tgccggatat gaccccgagc accgaaatga gcatgcgcgg cgtgcgcgtg | 1440 |
| agcaaaatgg gcgtggatga atatagcaac gcggaacgcg tggtggtgag cattgatcgc | 1500 |
| tttctgcgcg tgcgcgatca gcgcggcaac gtgctgctga gcccggaaga agtgagcgaa | 1560 |

```
acccagggca ccgaaaaact gaccattacc tatagcagca gcatgatgtg ggaaattaac    1620
ggcccggaaa gcgtgctgat taacacctat cagtggatta ttcgcaactg ggaaaccgtg    1680
aaaattcagt ggagccagaa cccgaccatg ctgtataaca aaatggaatt tgaaccgttt    1740
cagagcctgg tgccgaaagc gattcgcggc cagtatagcg gctttgtgcg caccctgttt    1800
cagcagatgc gcgatgtgct gggcaccttt gataccaccc agattattaa actgctgccg    1860
tttgcggcgg cgccgccgaa acagagccgc atgcagttta gcagcctgac cgtgaacgtg    1920
cgcggcagcg gcatgcgcat tctggtgcgc ggcaacagcc cggtgtttaa ctataacaaa    1980
accaccaaac gcctgaccgt gctgggcaaa gatgcgggca ccctgaccga agatccggat    2040
gaaggcaccg cgggcgtgga aagcgcggtg ctgcgcggct ttctgattct gggcaaagaa    2100
gatcgccgct atgccccggc gctgagcatt aacgaactga gcaacctggc gaaaggcgaa    2160
aaagcgaacg tgctgattgg ccagggcgat gtggtgctgg tgatgaaacg caaacgcgat    2220
agcagcattc tgaccgatag ccagaccgcg accaaacgca ttcgcatggc gattaac       2277
```

INFLUENZA VIRUS REASSORTMENT

This is a continuation of U.S. application Ser. No. 14/648,886, filed on Jun. 1, 2015, which is a national stage filing under 35 U.S.C. § 371 of International Application No. PCT/EP2013/075294, filed on Dec. 2, 2013, and claims the benefit of U.S. Provisional Application No. 61/732,809, filed on Dec. 3, 2012, all of which are incorporated herein by reference.

This invention was made in part with Government support under grant no. HHSO10020100061C awarded by the Biomedical Advanced Research and Development Authority (BARDA). The Government has certain rights in the invention.

TECHNICAL FIELD

This invention is in the field of influenza A virus reassortment. Furthermore, it relates to manufacturing vaccines for protecting against influenza A viruses.

BACKGROUND ART

The most efficient protection against influenza infection is vaccination against circulating strains and it is important to produce influenza viruses for vaccine production as quickly as possible.

Wild-type influenza viruses often grow to low titres in eggs and cell culture. In order to obtain a better-growing virus strain for vaccine production it is currently common practice to reassort the circulating vaccine strain with a faster-growing high-yield donor strain. This can be achieved by co-infecting a culture host with the circidating influenza strain (the vaccine strain) and the high-yield donor strain and selecting for reassortant viruses which contain the hemagglutinin (HA) and neuraminidase (NA) segments from the vaccine strain and the other viral segments (i.e. those encoding PB1, PB2, PA, NP, $M_1$, $M_2$, $NS_1$ and $NS_2$) from the donor strain. Another approach is to reassort the influenza viruses by reverse genetics (see, for example references 1 and 2).

Reference 3 reports that a reassortant influenza virus containing a PB1 gene segment from A/Texas/1/77, the HA and NA segments from A/New Caledonia/20/99, a modified PA segment derived from A/Puerto Rico/8/34 and the remaining viral segments from A/Puerto Rico/8/34 shows increased growth in cells.

There are currently only a limited number of donor strains for reassorting influenza viruses for vaccine manufacture, and the strain most commonly used is the A/Puerto Rico/8/34 (A/PR/8/34) strain. However, reassortant influenza viruses comprising A/PR/8/34 backbone segments do not always grow sufficiently well to ensure efficient vaccine manufacture. Thus, there is a need in the art to provide further and improved donor strains for influenza virus reassortment.

SUMMARY OF PREFERRED EMBODIMENTS

The inventors have now surprisingly discovered that influenza viruses which comprise backbone segments from two or more influenza donor strains can grow faster in a culture host (particularly in cell culture) compared with reassortant influenza A viruses which contain all backbone segments from the same donor strain. In particular, the inventors have found that influenza viruses which comprise backbone segments derived from two different high-yield donor strains can produce higher yield reassortants with target vaccine-relevant HA/NA genes than reassortants made with either of the two original donor strains alone.

Reassortant influenza A viruses with backbone segments from two or more influenza donor strains may comprise the HA segment and the PB1 segment from different influenza A strains. In these reassortant influenza viruses the PB1 segment is preferably from donor viruses with the same influenza virus HA subtype as the vaccine strain. For example, the PB1 segment and the HA segment may both be from influenza viruses with a H1 subtype. The reassortant influenza A viruses may also comprise the HA segment and the PB1 segment from different influenza A strains with different influenza virus HA subtypes, wherein the PB1 segment is not from an influenza virus with a H3 HA subtype and/or wherein the HA segment is not from an influenza virus with a H1 or H5 HA subtype. For example, the PB1 segment may be from a H1 virus and/or the HA segment may be from a H3 influenza virus.

The invention also provides reassortant influenza A viruses with backbone segments from two or more influenza donor strains in which the PB1 segment is from the A/California/07/09 influenza strain. This segment may have at least 95% identity or 100% identity with the sequence of SEQ ID NO: 22. The reassortant influenza A virus may have the H1 HA subtype. It will be understood that a reassortant influenza virus according to this aspect of the invention will not comprise the HA and/or NA segments from A/California/07/09.

Where the reassortant influenza A virus comprises backbone segments from two or three donor strains, each donor strain may provide more than one of the backbone segments of the reassortant influenza A virus, but one or two of the donor strains can also provide only a single backbone segment.

Where the reassortant influenza A virus comprises backbone segments from two, three, four or five donor strains, one or two of the donor strains may provide more than one of the backbone segments of the reassortant influenza A virus. In general the reassortant influenza A virus cannot comprise more than six backbone segments. Accordingly, for example, if one of the donor strains provides five of the viral segments, the reassortant influenza A virus can only comprise backbone segments from a total of two different donor strains.

Where a reassortant influenza A virus comprises the PB1 segment from A/Texas/1/77, it preferably does not comprise the PA, NP or M segment from A/Puerto Rico/8/34. Where a reassortant influenza A virus comprises the PA, NP or M segment from A/Puerto Rico/8/34, it preferably does not comprise the FBI segment from A/Texas/1/77. In some embodiments, the invention does not encompass reassortant influenza A viruses which have the PB1 segment from A/Texas/1/77 and the PA, NP and M segments from A/Puerto Rico/8/34. The PB1 segment from A/Texas/1/77 may have the sequence of SEQ ID NO: 27 and the PA, NP or M segments from A/Puerto Rico/8/34 may have the sequence of SEQ ID NOs 28, 29 or 30, respectively.

Influenza A virus strains of the invention can grow to higher viral titres in MDCK cells and/or in eggs in the same time and under the same growth conditions compared with reassortant influenza strains that comprise all backbone segments from the same influenza donor strain.

The invention also provides a reassortant influenza A virus comprising at least one backbone viral segment from a donor strain, wherein the donor strain is the A/California/07/09 influenza strain. When the at least one backbone viral segment is the PA segment it may have a sequence having at least 95% or at least 99% identity with the sequence of SEQ ID NO: 15. When the at least one backbone viral segment is the PB1 segment, it may have a sequence having at least 95% or at least 99% identity with the sequence of SEQ ID NO: 16. When the at least one backbone viral segment is the PB2 segment, it may have a sequence having at least 95% or at least 99% identity with the sequence of SEQ ID NO: 17. When the at least one backbone viral segment is the NP segment it may have a sequence having at least 95% or at least 99% identity with the sequence of SEQ ID NO: 18. When the at least one backbone viral segment is the M segment it may have a sequence having at least 95% or at least 99% identity with the sequence of SEQ ID NO: 19. When the at least one backbone viral segment is the NS segment it may have a sequence having at least 95% or at least 99% identity with the sequence of SEQ ID NO: 20.

At least one backbone segment may be derived from the A/California/07/09 influenza strain, as discussed in the previous paragraph. Preferred reassortant influenza A viruses comprise the PB1 segment from the A/California/07/09 influenza strain. The inventors have shown that reassortant influenza A viruses comprising this backbone segment grow well in culture hosts. The reassortant influenza A viruses may comprise all other backbone segments from an influenza virus which is not A/California/07/09.

The reassortant influenza A viruses may comprise the PB1 segment from A/California/07/09 and all other backbone segments from the influenza strain PR8-X. The segments of PR8-X have the sequences of SEQ ID NO: 1 (PA), SEQ ID NO: 2 (PB1), SEQ ID NO: 3 (PB2), SEQ ID NO: 4 (NP), SEQ ID NO: 5 (M), SEQ ID NO: 6 (NS), SEQ ID NO: 7 (HA) or SEQ ID NO: 8 (NA). Thus, the influenza viruses of the invention may comprise one or more genome segments selected from: a PA segment having at least 95% or 99% identity to the sequence of SEQ ID NO: 1, a PB2 segment having at least 95% or 99% identity to the sequence of SEQ ID NO: 3, a M segment having at least 95% or 99% identity to the sequence of SEQ ID NO: 5, a NP segment having at least 95% or 99% identity to the sequence of SEQ ID NO: 4, and/or a NS segment having at least 95% or 99% identity to the sequence of SEQ ID NO: 6. The reassortant influenza A viruses may also comprise one or more viral segments which have the sequence of SEQ ID NOs: 1, and/or 3-6. In preferred embodiments, the reassortant influenza strain comprises all of the genome segments mentioned in this paragraph. This embodiment is preferred because the inventors have found that such reassortant influenza A viruses grow particularly well in cell culture and in embryonated hens eggs.

In general a reassortant influenza virus will contain only one of each backbone segment. For example, when the influenza virus comprises the PB1 segment from A/California/07/09 it will not at the same time comprise the PB1 segment from another influenza A donor strain.

The backbone viral segments may be optimized for culture in the specific culture host. For example, where the reassortant influenza viruses are cultured in mammalian cells, it is advantageous to adapt at least one of the viral segments for optimal growth in the culture host. For example, where the expression host is a canine cell, such as a MDCK cell line, the viral segments may have a sequence which optimises viral growth in the cell. Thus, the reassortant influenza viruses of the invention may comprise a PB2 genome segment which has lysine in the position corresponding to amino acid 389 of SEQ ID NO: 3 when aligned to SEQ ID NO: 3 using a pairwise alignment algorithm, and/or asparagine in the position corresponding to amino acid 559 of SEQ ID NO: 3 when aligned to SEQ ID NO: 3 using a pairwise alignment algorithm. Also provided are reassortant influenza viruses in accordance with the invention in which the PA genome segment has lysine in the position corresponding to amino acid 327 of SEQ ID NO: 1 when aligned to SEQ ID NO: 1 using a pairwise alignment algorithm, and/or aspartic acid in the position corresponding to amino acid 444 of SEQ ID NO: 1 when aligned to SEQ ID NO: 1, using a pairwise alignment algorithm, and/or aspartic acid in the position corresponding to amino acid 675 of SEQ ID NO: 1 when aligned to SEQ ID NO: 1, using a pairwise alignment algorithm. The reassortant influenza strains of the invention may also have a NP genome segment with threonine in the position corresponding to amino acid 27 of SEQ ID NO: 4 when aligned to SEQ ID NO: 4 using a pairwise alignment algorithm, and/or asparagine in the position corresponding to amino acid 375 of SEQ ID NO: 4 when aligned to SEQ ID NO: 4, using a pairwise alignment algorithm. Variant influenza strains may also comprise two or more of these mutations. It is preferred that the variant influenza virus contains a variant PB2 segment with both of the amino acids changes identified above, and/or a PA which contains all three of the amino acid changes identified above, and/or a NP segment which contains both of the amino acid changes identified above. The influenza A virus may be a H1 strain.

Alternatively, or in addition, the reassortants influenza viruses may comprise a PB1 segment which has isoleucine in the position corresponding to amino acid 200 of SEQ ID NO: 2 when aligned to SEQ ID NO: 2 using a pairwise alignment algorithm, and/or asparagine in the position corresponding to amino acid 338 of SEQ ID NO: 2 when aligned to SEQ ID NO: 2 using a pairwise alignment algorithm, and/or isoleucine in the position corresponding to amino acid 529 of SEQ ID NO: 2 when aligned to SEQ ID NO: 2 using a pairwise alignment algorithm, and/or isoleucine in the position corresponding to amino acid 591 of SEQ ID NO: 2 when aligned to SEQ TD NO: 2 using a pairwise alignment algorithm, and/or histidine in the position corresponding to amino acid 687 of SEQ ID NO: 2 when aligned to SEQ ID NO: 2 using a pairwise alignment algorithm, and/or lysine in the position corresponding to amino acid 754 of SEQ ID NO: 2 when aligned to SEQ ID NO: 2 using a pairwise alignment algorithm.

The preferred pairwise alignment algorithm is the Needleman-Wunsch global alignment algorithm [4], using default parameters (e.g. with Gap opening penalty=10.0, and with Gap extension penalty=0.5, using the EBLOSUM62 scoring matrix). This algorithm is conveniently implemented in the needle tool in the EMBOSS package [5].

The invention provides a method of preparing the reassortant influenza A viruses of the invention. These methods comprise steps of (i) introducing into a culture host one or more expression construct(s) which encode(s) the viral segments required to produce an influenza A virus wherein the backbone viral segments are from two or more influenza strains; and (ii) culturing the culture host in order to produce reassortant virus and optionally (iii) purifying the virus obtained in step (ii). In these methods, the HA and the PB1 segment may be from different influenza strains which have the same influenza HA subtype or the HA and PB1 segments may be from different influenza strains with different HA subtypes provided that the PB1 segment is not from an influenza virus with a H3 HA subtype and/or the HA segment is not from an influenza virus with a H1 or H5 HA subtype. The PB1 backbone viral segment may be from A/California/07/09. The one or more expression constructs may further encode one or more of the PB2, PA, NP, M, or NS segments from PR8-X or segments having at least 90% or 100% identity to SEQ ID NOs: 9, and/or 11 to 14. The expression construct(s) may not encode the HA and/or NA segments from A/California/07/09 when the PB1 segment is from A/California/07/09.

The at least one expression construct may comprise a sequence having at least 90%, at least 95%, at least 99% or 100% identity with the sequence of SEQ ID NO: 22.

In some embodiments, the at least one expression construct does not encode the PB1 segment from the A/Texas/1/77 influenza strain.

The methods may further comprise steps of: (iv) infecting a culture host with the virus obtained in step (ii) or step (iii); (v) culturing the culture host from step (iv) to produce further virus; and optionally (vi) purifying the virus obtained in step (v).

The invention also provides a method for producing influenza viruses comprising steps of (a) infecting a culture host with a reassortant virus of the invention; (b) culturing the host from step (a) to produce the virus; and optionally (c) purifying the virus obtained in step (b).

The invention also provides a method of preparing a vaccine, comprising steps of (d) preparing a virus by the methods of any one of the embodiments described above and (e) preparing vaccine from the virus.

The invention provides an expression system comprising one or more expression construct(s) comprising the vRNA encoding segments of an influenza A virus wherein the expression construct(s) encode(s) the HA and PB1 segments from two different influenza strains with the same influenza HA subtype or which encodes the HA and PB1 segments from two different influenza strains with different influenza virus HA subtypes, wherein the PB1 segment is not from an influenza virus with a H3 HA subtype and/or the HA segment is not from an influenza virus with a H1 or H5 HA subtype.

The invention also provides an expression system comprising one or more expression construct(s) comprising the vRNA encoding segments of an influenza A virus wherein the expression construct(s) encode(s) the FBI segment of A/California/07/09. The expression construct(s) may further comprise the vRNAs which encode one or more of the PB2, NP, NS, M and/or PA segments from PR8-X. Thus, the expression construct(s) may comprise one or more nucleotide sequences having at least 90% identity, at least 95% identity, at least 99% identity or 100% identity with the sequences of SEQ ID NOs: 9 and/or 11-14. It is preferred that the expression construct(s) encode(s) all of the PB2, NP, NS, M and PA segments from PR8-X.

The invention also provides a host cell comprising the expression systems of the invention. These host cells can express an influenza A virus from the expression construct(s) in the expression system.

Expression constructs which can be used in the expression systems of the invention are also provided. For example, the invention provides an expression construct which encodes the backbone segments of the reassortant influenza strains according to the invention on the same construct.

Donor Strains

Influenza donor strains are strains which typically provide the backbone segments in a reassortant influenza virus, even though they may sometimes also provide the NA segment of the virus. Usually, however, both the HA and the NA segment in a reassortant influenza virus will be from the vaccine strain which is the influenza strain that provides the HA segment.

The inventors have surprisingly discovered that reassortant influenza A viruses which comprise the HA segment and the PB1 segment from different influenza A strains with the same HA subtype can grow much faster in culture hosts compared with reassortant influenza viruses which comprise the HA and PB1 segments from viruses with different HA subtypes. These reassortant influenza viruses preferably have backbone segments from at least two donor strains.

The PB1 segments of influenza viruses with the same HA subtype will usually have a higher level of identity than the PB1 segments of influenza viruses with different HA subtypes. For example, a Blast search using the PB1 segment of the H1 strain A/California/07/09 showed that only influenza strains with the H1 HA subtype had a high identity in the PB1 segment. Likewise, a Blast search using the PB1 segment of the H3 strain A/Wisconsin/67/2005 showed that only influenza viruses with the H3 HA subtype had a high level of identity to the PB1 segment of this virus.

The inventors have further discovered that reassortant influenza A viruses which have backbone segments from at least two donor strains and comprise the PB1 segment from A/California/07/09 grow particularly well in culture hosts. These reassortant influenza viruses preferably have backbone segments from at least two different donor strains. The reassortant influenza viruses may comprise the PB1 segment from A/California/07/09 and the HA segment of an influenza virus with the H1 subtype.

Influenza strains which contain one, two, three, four five, six or seven of the segments of the A/California/07/09 strain can also be used as donor strains.

The invention can be practised with donor strains having a viral segment that has at least about 70%, at least about 75%, at least about 80%, at least about 85%, at least about 90%, at least about 95% or at least about 99% identity to a sequence of SEQ ID NOs 9-14 or 21-26. For example, due to the degeneracy of the genetic code, it is possible to have the same polypeptide encoded by several nucleic acids with different sequences. Thus, the invention may be practised with viral segments that encode the same polypeptides as the sequences of SEQ ID NOs 1-8 or 15-20. For example, the nucleic acid sequences of SEQ ID NOs: 31 and 32 have only 73% identity even though they encode the same viral protein.

The invention may also be practised with viral segments that encode polypeptides that have at least 80%, at least 85%, at least 90%, at least 95% or at least 99% identity to the polypeptide sequences encoded by SEQ ID NOs 9-22.

Variations in the DNA and the amino acid sequence may also stem from spontaneous mutations which can occur during passaging of the viruses. Such variant influenza strains can also be used in the invention.

Reassortant Viruses

The invention provides reassortant influenza viruses which comprise backbone segments from two or more influenza donor strains. These reassortant influenza viruses may comprise the HA segment and the PB1 segment from different influenza A strains provided that the HA and the PB1 segments are from influenza viruses with the same influenza virus HA subtype. They may also comprise the HA segment and the PB1 segment from different influenza A strains with different influenza virus HA subtypes, provided that the PB1 segment is not from an influenza virus with a H3 HA subtype and/or the HA segment is not from an influenza virus with a H1 or H5 HA subtype.

Further provided are reassortant influenza viruses with backbone segments from two or more different donor strains which comprise the PB1 segment from A/California/07/09.

The PB1 and PB2 segments may be from the same donor strain.

Influenza viruses are segmented negative strand RNA viruses. Influenza A and B viruses have eight segments (NP, M, NS, PA, PB1, HA and NA) whereas influenza C virus has seven. The reassortant viruses of the invention contain the backbone segments from two or more donor strains, or at least one (i.e. one, two, three, four, five or six) backbone viral segment from A/California/07/09. The backbone viral segments are those which do not encode HA or NA. Thus, backbone segments will typically encode the PB1, PB2, PA, NP, $M_1$, $M_2$, $NS_1$ and $NS_2$ polypeptides of the influenza virus.

The viruses may also contain an NS segment that does not encode a functional NS protein as described, for example, in reference 6. The reassortant viruses will not typically contain the segments encoding HA and NA from the donor strains even though reassortant viruses which comprise either the HA or the NA but not both from the donor strains of the invention are also envisioned.

When the reassortant viruses are reassortants comprising the backbone segments from a single donor strain, the reassortant viruses will generally include segments from the donor strain and the vaccine strain in a ratio of 1:7, 2:6, 3:5, 4:4, 5:3, 6:2 or 7:1. Having a majority of segments from the donor strain, in particular a ratio of 6:2, is typical. When the reassortant viruses comprise backbone segments from two donor strains, the reassortant virus will generally include segments from the first donor strain, the second donor strain and the vaccine strain in a ratio of 1:1:6, 1:2:5, 1:3:4, 1:4:3, 1:5:2, 1:6:1, 2:1:5, 2:2:4, 2:3:3, 2:4:2, 2:5:1, 3:1:2, 3:2:1, 4:1:3, 4:2:2, 4:3:1, 5:1:2, 5:2:1 or 6:1:1.

Preferably, the reassortant viruses do not contain the HA segment of the donor strain as this encodes the main vaccine antigens of the influenza virus and should therefore come from the vaccine strain. The reassortant viruses of the invention therefore preferably have at least the HA segment and typically the HA and NA segments from the vaccine strain.

The invention also encompasses reassortants which comprise viral segments from more than one vaccine strain provided that the reassortant comprises a backbone according to the present invention. For example, the reassortant influenza viruses may comprise the HA segment from one donor strain and the NA segment from a different donor strain.

The reassortant viruses of the invention can grow to higher viral titres than the wild-type vaccine strain from which some of the viral segment(s) of the reassortant virus are derived in the same time (for example 12 hours, 24 hours, 48 hours or 72 hours) and under the same growth conditions. The viral titre can be determined by standard methods known to those of skill in the art. The reassortant viruses of the invention can achieve a viral titre which is at least 10% higher, at least 20% higher, at least 50% higher, at least 100% higher, at least 200% higher, at least 500% higher, or at least 1000% higher than the viral titre of the wild type vaccine strain in the same time frame and under the same conditions.

The invention is suitable for reassorting pandemic as well as inter-pandemic (seasonal) influenza vaccine strains. The reassortant influenza strains may contain the influenza A virus HA subtypes H1, H2, H3, H4, H5, H6, H7, H8, H9, H10, H11, H12, H13, H14, H15 or H16. They may contain the influenza A virus NA subtypes N1, N2, N3, N4, N5, N6, N7, N8 or N9. Where the vaccine strain used in the reassortant influenza viruses of the invention is a seasonal influenza strain, the vaccine strain may have a H1 or H3 subtype. In one aspect of the invention the vaccine strain is a H1N1 or H3N2 strain. The reassortants influenza strains may also contain the HA segment of an influenza B strain.

The vaccine strains for use in the invention may also be pandemic strains or potentially pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naive to the strain's hemagglutinin; (b) it is capable of being transmitted horizontally in the human population; and (c) it is pathogenic to humans. A vaccine strain with a H5 hemagglutinin type is preferred where the reassortant virus is used in vaccines for immunizing against pandemic influenza, such as a H5N1 strain. Other possible strains include H5N3, H9N2, H2N2, H7N1 and H7N7, and any other emerging potentially pandemic strains. The invention is particularly suitable for producing reassortant viruses for use in a vaccine for protecting against potential pandemic virus strains that can or have spread from a non-human animal population to humans, for example a swine-origin H1N1 influenza strain.

The reassortant influenza strain of the invention may comprise the HA segment and/or the NA segment from an A/California/4/09 strain.

Strains which can be used as vaccine strains include strains which are resistant to antiviral therapy (e.g. resistant to oscltamivir [7] and/or zanamivir), including resistant pandemic strains [8].

Reassortant viruses which contain an NS segment that does not encode a functional NS protein are also within the scope of the present invention. NS1 knockout mutants are described in reference 6. These NS 1-mutant virus strains are particularly suitable for preparing live attenuated influenza vaccines.

The 'second influenza strain' used in the methods of the invention is different to the donor strain which is used.

Reverse Genetics

The invention is particularly suitable for producing the reassortant influenza virus strains of the invention through reverse genetics techniques. In these techniques, the viruses are produced in culture hosts using an expression system.

In one aspect, the expression system may encode the HA and PB1 segment from different influenza strains with the same HA subtype. It may also encode the HA and PB1 segments from different influenza strains with different HA subtypes provided that the PB1 segment is not from an influenza virus with a H3 HA subtype and/or the HA segment is not from an influenza virus with a H1 or H5 HA subtype. The expression system may encode the PB1 segment from A/California/07/09. In these embodiments, the system may encode at least one of the segments NP, M, NS, PA, and/or PB2 from another influenza donor strain, for example PR8-X.

Reverse genetics for influenza A and B viruses can be practised with 12 plasmids to express the four proteins required to initiate replication and transcription (PB1, PB2, PA and nucleoprotein) and all eight viral genome segments. To reduce the number of constructs, however, a plurality of RNA polymerase I transcription cassettes (for viral RNA synthesis) can be included on a single plasmid (e.g. sequences encoding 1, 2, 3, 4, 5, 6, 7 or all 8 influenza vRNA segments), and a plurality of protein-coding regions with RNA polymerase II promoters on another plasmid (e.g. sequences encoding 1, 2, 3, 4, 5, 6, 7 or 8 influenza mRNA transcripts) [9]. It is also possible to include one or more influenza vRNA segments under control of a pol I promoter and one or more influenza protein coding regions under control of another promoter, in particular a pol II promoter, on the same plasmid. This is preferably done by using bi-directional plasmids.

Preferred aspects of the reference 9 method involve: (a) PB1, PB2 and PA mRNA-encoding regions on a single expression construct; and (b) all 8 vRNA encoding segments on a single expression construct. Including the neuraminidase (NA) and hemagglutinin (HA) segments on one expression construct and the six other viral segments on another expression construct is particularly preferred as newly emerging influenza virus strains usually have mutations in the NA and/or HA segments. Therefore, the advantage of having the HA and/or NA segments on a separate expression construct is that only the vector comprising the HA and NA sequence needs to be replaced. Thus, in one aspect of the invention the NA and/or HA segments of the vaccine strain may be included on one expression construct and the vRNA encoding segments from the donor strain(s) of the invention, excluding the HA and/or NA segment(s), are included on a different expression construct. The invention thus provides an expression construct comprising one, two, three, four, five or six vRNA encoding backbone viral segments of a donor strain of the invention. The expression construct may not comprise HA and/or NA viral segments that produce a functional HA and/or NA protein.

Known reverse genetics systems involve expressing DNA molecules which encode desired viral RNA (vRNA) molecules from pol 1 promoters, bacterial RNA polymerase promoters, bacteriophage polymerase promoters, etc. As influenza viruses require the presence of viral polymerase to initiate the life cycle, systems may also provide these proteins e.g. the system further comprises DNA molecules that encode viral polymerase proteins such that expression of both types of DNA leads to assembly of a complete infectious virus. It is also possible to supply the viral polymerase as a protein.

Where reverse genetics is used for the expression of influenza vRNA, it will be evident to the person skilled in the art that precise spacing of the sequence elements with reference to each other is important for the polymerase to initiate replication. It is therefore important that the DNA molecule encoding the viral RNA is positioned correctly between the pol 1 promoter and the termination sequence, but this positioning is well within the capabilities of those who work with reverse genetics systems.

In order to produce a recombinant virus, a cell must express all segments of the viral genome which are necessary to assemble a virion. DNA cloned into the expression constructs of the present invention preferably provides all of the viral RNA and proteins, but it is also possible to use a helper virus to provide some of the RNA and proteins, although systems which do not use a helper virus are preferred. As the influenza virus is a segmented virus, the viral genome will usually be expressed using more than one expression construct in the methods of the invention. It is also envisioned, however, to combine one or more segments or even all segments of the viral genome on a single expression construct.

In some embodiments an expression construct will also be included which leads to expression of an accessory protein in the host cell. For instance, it can be advantageous to express a non-viral serine protease (e.g. trypsin) as part of a reverse genetics system.

Expression Constructs

Expression constructs used in the expression systems of the invention may be uni-directional or bi-directional expression constructs. Where more than one transgene is used in the methods (whether on the same or different expression constructs) it is possible to use uni-directional and/or bi-directional expression.

As influenza viruses require a protein for infectivity, it is generally preferred to use bi-directional expression constructs as this reduces the total number of expression constructs required by the host cell. Thus, the method of the invention may utilise at least one bi-directional expression construct wherein a gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped vRNAs while the pol II promoter can be used to transcribe mRNAs which can subsequently be translated into proteins, thus allowing simultaneous expression of RNA and protein from the same construct. Where more than one expression construct is used within an expression system, the promoters may be a mixture of endogenous and non-endogenous promoters.

The pol I and pol II promoters used in the expression constructs may be endogenous to an organism from the same taxonomic order from which the host cell is derived. Alternatively, the promoters can be derived from an organism in a different taxonomic order than the host cell. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora). For example, the human pol I promoter can be used to express viral segments in canine cells (e.g. MDCK cells) [10].

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression system may contain at least two, at least three, at least four, at least five, at least six, at least seven, at least eight, at least nine, at least ten, at least eleven or at least twelve expression constructs.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

As an alternative, an expression construct may be a linear expression construct. Such linear expression constructs will typically not contain any amplification and/or selection sequences. However, linear constructs comprising such amplification and/or selection sequences are also within the scope of the present invention. Reference 11 describes a linear expression construct which describes individual linear expression constructs for each viral segment. It is also possible to include more than one, for example two, three four, five or six viral segments on the same linear expression construct. Such a system has been described, for example, in reference 12.

Expression constructs can be generated using methods known in the art. Such methods were described, for example, in reference 13. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

The expression constructs used in the systems of the invention may be non-bacterial expression constructs. This means that the construct can drive expression in a eukaryotic cell of viral RNA segments encoded therein, but it does not include components which would be required for propagation of the construct in bacteria. Thus the construct will not include a bacterial origin of replication (ori), and usually will not include a bacterial selection marker (e.g. an antibiotic resistance marker). Such expression constructs are described in reference 14 which is incorporated by reference.

The expression constructs may be prepared by chemical synthesis. The expression constructs may either be prepared entirely by chemical synthesis or in part. Suitable methods for preparing expression constructs by chemical synthesis are described, for example, in reference 14 which is incorporated by reference.

The expression constructs of the invention can be introduced into host cells using any technique known to those of skill in the art. For example, expression constructs of the invention can be introduced into host cells by employing electroporation, DEAE-dextran, calcium phosphate precipitation, liposomes, microinjection, or microparticle-bombardment.

Cells

The culture host for use in the present invention can be any eukaryotic cell that can produce the virus of interest. The invention will typically use a cell line although, for example, primary cells may be used as an alternative. The cell will typically be mammalian or avian. Suitable mammalian cells include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [15-17]. Suitable dog cells are e.g. kidney cells, as in the CLDK and MDCK cell lines.

Further suitable cells include, but are not limited to: CHO; 293T; BHK; MRC 5; PER.C6 [18]; FRhL2; WI-38; etc. Suitable cells are widely available e.g. from the American Type Cell Culture (ATCC) collection [19], from the Coriell Cell Repositories [20], or from the European Collection of Cell Cultures (ECACC). For example, the ATCC supplies various different Vero cells under catalogue numbers CCL 81, CCL 81.2, CRL 1586 and CRE-1587, and it supplies MDCK cells under catalogue number CCL 34. PER.C6 is available from the ECACC under deposit number 96022940.

Preferred cells for use in the invention are MDCK cells [21-23], derived from Madin Darby canine kidney. The original MDCK cells are available from the ATCC as CCL 34. It is preferred that derivatives of MDCK cells are used. Such derivatives were described, for instance, in reference 21 which discloses MDCK cells that were adapted for growth in suspension culture ('MDCK 33016' or '33016-PF', deposited as DSM ACC 2219; see also ref. 21). Furthermore, reference 24 discloses MDCK-derived cells that grow in suspension in serum free culture ('B-702', deposited as FERM BP-7449). In some embodiments, the MDCK cell line used may be tumorigenic. It is also envisioned to use non-tumorigenic MDCK cells. For example, reference 25 discloses non tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (ATCC PTA-6503). Reference 26 discloses MDCK cells with high susceptibility to infection, including 'MDCK.5F1' cells (ATCC CRL 12042).

It is possible to use a mixture of more than one cell type to practise the methods of the present invention. However, it is preferred that the methods of the invention are practised with a single cell type e.g. with monoclonal cells. Preferably, the cells used in the methods of the present invention are from a single cell line. Furthermore, the same cell line may be used for reassorting the virus and for any subsequent propagation of the virus.

Preferably, the cells are cultured in the absence of serum, to avoid a common source of contaminants. Various serum-free media for eukaryotic cell culture are known to the person skilled in the art (e.g. Iscove's medium, ultra CHO medium (BioWhittaker), EX-CELL (JRH Biosciences)). Furthermore, protein-free media may be used (e.g. PF-CHO (JRH Biosciences)). Otherwise, the cells for replication can also be cultured in the customary serum-containing media (e.g. MEM or DMEM medium with 0.5% to 10% of fetal calf serum).

The cells may be in adherent culture or in suspension.

Conventional Reassortment

Traditionally, influenza viruses are reassorted by co-infecting a culture host, usually eggs, with a donor strain and a vaccine strain. Reassortant viruses are selected by adding antibodies with specificity for the HA and/or NA proteins of the donor strain in order to select for reassortant viruses that contain the vaccine strain's HA and/or NA proteins. Over several passages of this treatment one can select for fast growing reassortant viruses containing the vaccine strain's HA and/or NA segments.

The invention is suitable for use in these methods. It can be easier to use vaccine strains with a different HA and/or NA subtype compared to the donor strain(s) as this facilitates selection for reassortant viruses. It is also possible, however, to use vaccine strains with the same HA and/or NA subtype as the donor strain(s) and in some aspects of the invention this preferred. In this case, antibodies with preferential specificity for the HA and/or NA proteins of the donor strain(s) should be available.

Virus Preparation

In one embodiment, the invention provides a method for producing influenza viruses comprising steps of (a) infecting a culture host with a reassortant virus of the invention; (b) culturing the host from step (a) to produce the virus; and optionally (c) purifying the virus produced in step (b).

The culture host may be cells or embryonated hen eggs. Where cells are used as a culture host in this aspect of the invention, it is known that cell culture conditions (e.g. temperature, cell density, pH value, etc.) are variable over a wide range subject to the cell line and the virus employed and can be adapted to the requirements of the application. The following information therefore merely represents guidelines.

As mentioned above, cells are preferably cultured in serum-free or protein-free media.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. When culturing the infected cells (step b), the cells are preferably cultured at a temperature of between 30° C. and 36° C. or between 32° C. and 34° C. or at 33° C. This is particularly preferred, as it has been shown that incubation of infected cells in this temperature range results in production of a virus that results in improved efficacy when formulated into a vaccine [27].

Oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8-25 \times 10^5$ cells/mL in the batch system or preferably about $5-20 \times 10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Virus may be grown on cells in adherent culture or in suspension. Microcarrier cultures can be used. In some embodiments, the cells may thus be adapted for growth in suspension.

The methods according to the invention also include harvesting and isolation of viruses or the proteins generated by them. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The culture host may be eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa.

Vaccine

The invention utilises virus produced according to the method to produce vaccines.

Vaccines (particularly for influenza virus) are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated virus is used, the vaccine may comprise whole virion, split virion, or purified surface antigens (for influenza, including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 28-33, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxycthanols, NP9, quaternary ammonium compounds, sarcosyl, CTABs (cetyl trim ethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLU SHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [34] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The methods of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 35). Live virus vaccines include MedImmune's FLUMIST™ product (trivalent live virus vaccine).

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and c have been used, as have higher doses (e.g. 3× or 9× doses [36,37]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

Influenza strains used with the invention may have a natural HA as found in a wild-type virus, or a modified HA. For instance, it is known to modify HA to remove determinants (e.g. hyper-basic regions around the HA1/HA2 cleavage site) that cause a virus to be highly pathogenic in avian species. The use of reverse genetics facilitates such modifications.

As well as being suitable for immunizing against inter-pandemic strains, the compositions of the invention are particularly useful for immunizing against pandemic or potentially-pandemic strains. The invention is suitable for vaccinating humans as well as non-human animals.

Other strains whose antigens can usefully be included in the compositions are strains which are resistant to antiviral therapy (e.g. resistant to oseltamivir [38] and/or zanamivir), including resistant pandemic strains [39].

Compositions of the invention may include antigen(s) from one or more (e.g. 1, 2, 3, 4 or more) influenza virus strains, including influenza A virus and/or influenza B virus provided that at least one influenza strain is a reassortant influenza strain of the invention. Compositions wherein at least two, at least three or all of the antigens are from reassortant influenza strains of the invention are also envisioned. Where a vaccine includes more than one strain of influenza, the different strains are typically grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [40], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). As described below, adjuvants may also be included. A thorough discussion of such components is available in reference 41.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 μg/ml) mercurial material e.g. thiomersal-free [32, 42]. Vaccines containing no mercury are more preferred. An α-tocopherol succinate can be included as an alternative to mercurial compounds [32], Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [43], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 44 & 45, involving a two-step treatment, first using a DNase (e.g. Benzonase), which may be used during viral growth, and then a cationic detergent (e.g. CTAB), which may be used during virion disruption. Treatment with an alkylating agent, such as (j-propiolactone, can also be used to remove host cell DNA, and advantageously may also be used to inactivate virions [46].

Adjuvants

Compositions of the invention may advantageously include an adjuvant, which can function to enhance the immune responses (humoral and/or cellular) elicited in a subject who receives the composition. Preferred adjuvants comprise oil-in-water emulsions. Various such adjuvants are known, and they typically include at least one oil and at least one surfactant, with the oil(s) and surfactant(s) being biodegradable (metabolisable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Another preferred oil is α-tocopherol (see below).

Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)poly ethoxy ethanol (IGEPAL CA-630/NP-40); phospholipids such as phosphatidylcholine (lecithin); nonylphenol ethoxy lates, such as the Tergitolm NP series; polyoxy ethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Where the vaccine contains a split virus, it is preferred that it contains free surfactant in the aqueous phase. This is advantageous as the free surfactant can exert a 'splitting effect' on the antigen, thereby disrupting any unsplit virions and/or virion aggregates that might otherwise be present. This can improve the safety of split virus vaccines [47].

Preferred emulsions have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [48-50], as described in more detail in Chapter 10 of ref. 51 and chapter 12 of ref. 52. The MF59 emulsion advantageously includes citrate ions e.g. 10 mM sodium citrate buffer.

An emulsion comprising squalene, a tocopherol, and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g. 0.90) as this can provide a more stable emulsion. Squalene and polysorbate 80 may be present in a volume ratio of about 5:2 or at a weight ratio of about 11:5. Thus the three components (squalene, tocopherol, polysorbate 80) may be present at a weight ratio of 1068:1186:485 or around 55:61:25. One such emulsion ('AS03') can be made by dissolving Tween 80 in PBS to give a 2% solution, then mixing 90 ml of this solution with a mixture of (5 g of DL α tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [53] e.g. in the ratios discussed above.

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an a-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [54] (0.05-1% Thr-MDP, 5% squalane, 2.5% Pluronic L121 and 0.2% polysorbate 80). It can also be used without the Thr-MDP, as in the "AF" adjuvant [55] (5% squalane, 1.25% Pluronic Ll21 and 0.2% polysorbate 80). Microfluidisation is preferred.

An emulsion comprising squalene, an aqueous solvent, a polyoxyethylene alkyl ether hydrophilic nonionic surfactant (e.g. polyoxy ethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [56]. The emulsion may also include one or more of: alditol; a cryoprotective agent (e.g. a sugar, such as dodecylmaltoside and/or sucrose); and/or an alkylpolyglycoside. The emulsion may include a TLR4 agonist [57], Such emulsions may be lyophilized.

An emulsion of squalene, poloxamer 105 and Abil-Care [58]. The final concentration (weight) of these components in adjuvanted vaccines are 5% squalene, 4% poloxamer 105 (pluronic polyol) and 2% Abil-Care 85 (Bis-PEG/PPCi-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 59, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 60, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion in which a saponin (e.g. QuilA or QS21) and a sterol (e.g. a cholesterol) are associated as helical micelles [61].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [62].

An emulsion comprising a mineral oil, a non-ionic hydrophilic ethoxylated fatty alcohol, and a non-ionic lipophilic surfactant (e.g. an ethoxylated fatty alcohol and/or polyoxyethylene-polyoxypropylene block copolymer) [62].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g.

between 5:1 and 1:5) but is generally about 1:1. Where concentrations of components are given in the above descriptions of specific emulsions, these concentrations are typically for an undiluted composition, and the concentration after mixing with an antigen solution will thus decrease.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs or birds, and the invention provides a method of raising an immune response in a subject, comprising the step of administering a composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [63]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [64-66], oral [67], intradermal [68,69], transcutaneous, transdermal [70], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1) ≥70% seroprotection; (2) ≥40% seroconversion; and/or (3) a GMT increase of ≥2.5-fold. In elderly (>60 years), these criteria are: (1) ≥60% seroprotection; (2) ≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naive patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(I-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

The various steps of the methods may be carried out at the same or different times, in the same or different geographical locations, e.g. countries, and by the same or different people or entities.

Where animal (and particularly bovine) materials are used in the culture of cells, they should be obtained from sources that are free from transmissible spongiform encephalopathies (TSEs), and in particular free from bovine spongiform encephlialopathy (BSE). Overall, it is preferred to culture cells in the total absence of animal-derived materials.

Where a compound is administered to the body as part of a composition then that compound may alternatively be replaced by a suitable prodrug.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of reference 71. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is taught in reference 72.

References to a percentage sequence identity between two nucleic acid sequences mean that, when aligned, that percentage of bases are the same in comparing the two sequences. This alignment and the percent homology or sequence identity can be determined using software programs known in the art, for example those described in section 7.7.18 of reference 71. A preferred alignment program is GCG Gap (Genetics Computer Group, Wisconsin, Suite Version 10.1), preferably using default parameters, which are as follows: open gap=3; extend gap=1.

BRIEF DESCRIPTION OF THE DRAWINGS

FIG. 1(A)) or a second pandemic-like strain (strain 2; FIG. 1(B)). In FIG. 1(A) and FIG. 1(B), the white bar represents a reference vaccine strain (derived from WHO-Collaborating Centresents the average of the individual data points. The y-axis indicates infectious units/ml.

In FIG. 8(A), the dotted line with triangle markers indicates the PR8-X backbone and the solid line with square markers indicates a modified PR8-X backbone "PRS-X(cPA)" containing three canine-adapted mutations (E327K, N444D, and N675D) in the PR8-X PA segment. In FIG. 8(B), the dotted line with triangle markers indicates the PR8-X backbone and the solid line with open circle markers indicates a modified PR8-X backbone "PR8-X(cNP)" containing two canine-adapted mutations (A27T, E375N) in the PR8-X NP segment. In both figures, the x-axis indicates hours post-infection and the y-axis indicates infectious units/ml.

FIG. 9(A)) and HA titers (determined by red blood cell hemagglutination assay; FIG. 9(B)) of virus harvested at different times post-infection from MDCK cells infected with a reference vaccine strain or reverse genetics-derived 6:2 reassortant viruses made with either the PR8-X or modified PR8-X backbones containing canine-adapted mutations and the HA and NA segments from an H3 strain (strain 2). In FIG. 9(A), the dotted line with x markers indicates the reference vaccine strain (derived from WHO-Collaborating Centre-supplied strain), the dotted line with triangle markers indicates the PR8-X backbone, the solid line with square markers indicates a modified PR8-X backbone "PR8-X (cPA)" containing three canine-adapted mutations (E327K, N444D, and N675D) in the PR8-X PA segment, and the solid line with open circle markers indicates a modified PR8-X backbone "PR8-X (cNP)" containing two canine-adapted mutations a in the PR8-X NP segment. The y-axis represents infectious units/ml and the x-axis represents hours post-infection. In FIG. 9(B), the white bar indicates the reference vaccine strain (derived from WHO-Collaborating Centre-supplied strain), the dotted bar indicates the PR8-X backbone, the checked bar indicates the PRB-X(cPA) backbone and the cross-hatched bar indicates the PR8-X(cNP) backbone. The y-axis represents HA units from the 60 h post-infection time-point.

FIG. 10(A)) or a second H3 strain (strain 3; FIG. 10(B)) or a third H3 strain (strain 4; FIG. 10(C)). In FIG. 10(A) and FIG. 10(B), the white bar represents a reference vaccine strain (derived from WHO—Collaborating Centre-supplied strain) as control, the dotted bar represents a reassortant virus containing the PR8-X backbone, and the checked bar represents a reassortant virus containing the #21 backbone. The y-axis indicates HA yield in µg/ml.

MODES FOR CARRYING OUT THE INVENTION

Development of New Donor Strains

In order to provide high-growth donor strains, the inventors found that a reassortant influenza virus comprising the PB1 segment of A/California/07/09 and all other backbone segments from PR8-X shows improved growth characteristics compared with reassortant influenza viruses which contain all backbone segments from PR8-X. This influenza backbone is referred to as #21.

Focus-Forming Assays (FFA)

For the FFA, uninfected MDCK cells are plated at a density of 1.8×104 cells/well in 96 well plates in 100 pi of DMEM with 10% FCS. The next day, medium is aspirated and cells are infected with viruses in a volume of 50 pi (viruses diluted in DMEM+1% FCS). The cells are incubated at 37° C. until the next day.

At several time points after infection, the medium is aspirated and the cells washed once with PBS. 50 µl of ice-cold 50%150% acetone-methanol is added to each well followed by incubation at −20° C. for 30 minutes. The acetone mix is aspirated and the cells washed once with PBST (PBS+0.1% Tween). 50 µl of 2% BSA in PBS is added to each well followed by incubation at room temperature (RT) for 30 minutes. 50 µl of a 1:6000 dilution of anti-NP is added in blocking buffer followed by incubation at RT for 1 hours. The antibody solution is aspirated and the cells washed three times with PBST. Secondary antibody (goat anti mouse) is added at a dilution 1:2000 in 50 µl blocking buffer and the plate is incubated at RT for 1 hours. The antibody solution is aspirated and the cells washed three times with PBST. 50 µl of KPL True Blue is added to each well and incubated for 10 minutes. The reaction is stopped by aspirating the True-Blue and washing once with dH$_2$O. The water is aspirated and the cells are left to dry.

Growth Characteristics of Reassortant Viruses Containing PR8-X or #21 Backbones

In order to test the suitability of the #21 strain as a donor strain for virus reassortment, reassortant influenza viruses are produced by reverse genetics which contain the HA and NA proteins from various influenza strains (including zoonotic, seasonal, and pandemic-like strains) and the other viral segments from either PR8-X or the #21 backbone. The HA content, HA yield and the viral titres of these reassortant viruses are determined. As a control a reference vaccine strain which does not contain any backbone segments from PR8-X or A/California/07/09 is used. These viruses are cultured either in embyronated chicken eggs or in MDCK cells.

Figure 1A:
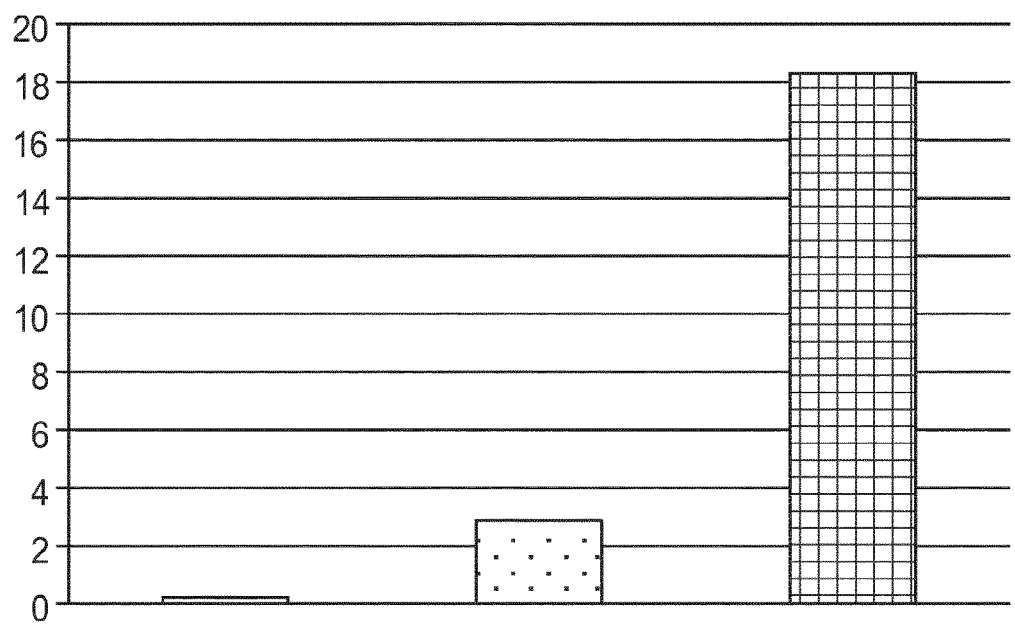
FIG. 1(A) and FIG. 1(B) compare the HA content (determined by lectin-capture ELISA) of sucrose gradient-purified viruses harvested at 60 h post-infection from MDCK cell cultures infected with reverse genetics-derived 6:2 reassortants containing either the PR8-X or #21 backbone with the HA and NA segments from a pandemic-like H1 strain (strain 1.
Figure 1B:
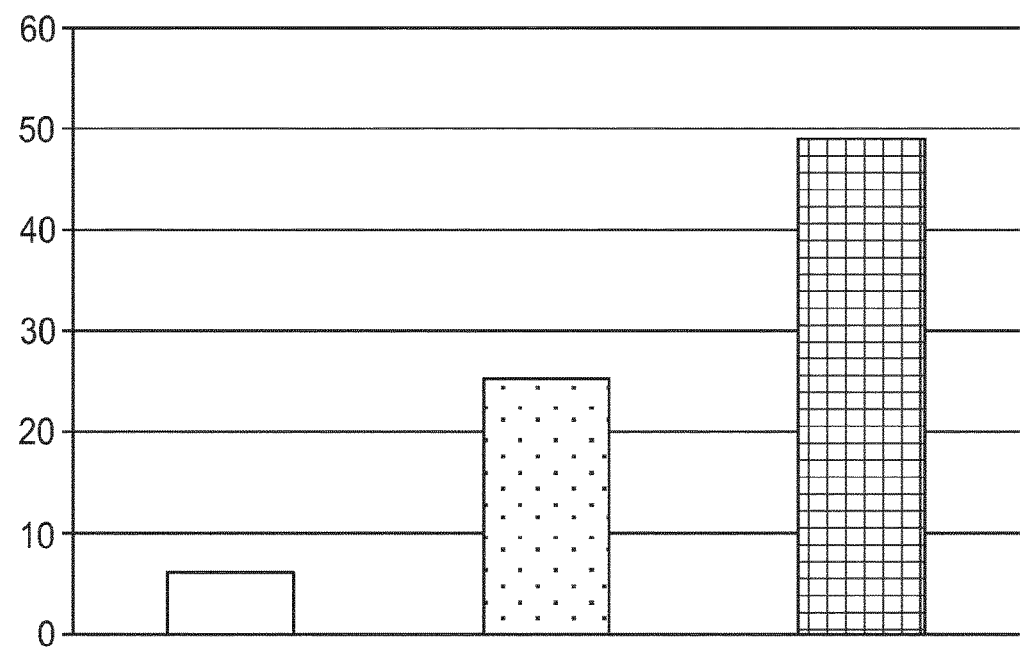
Figure 2A:
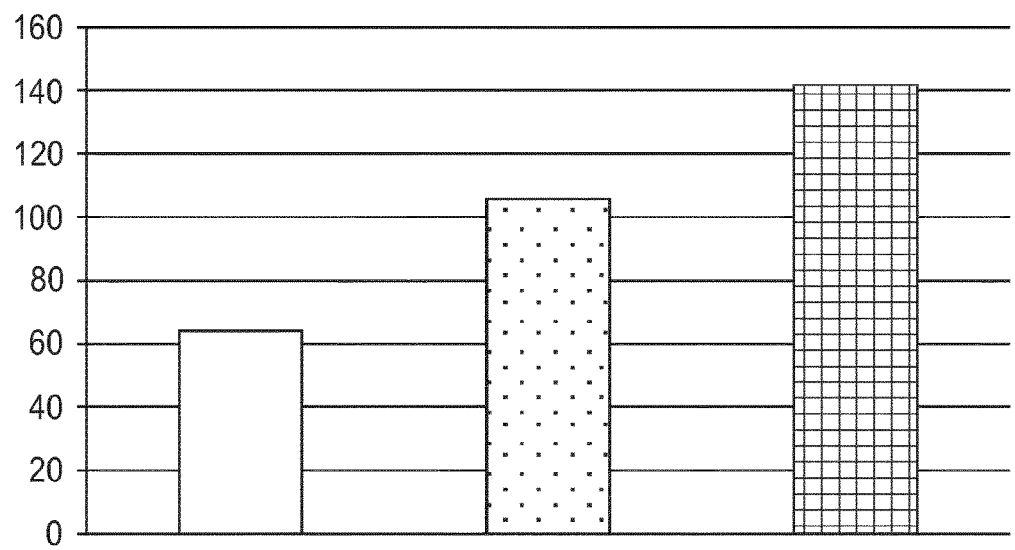
Figure 2B:
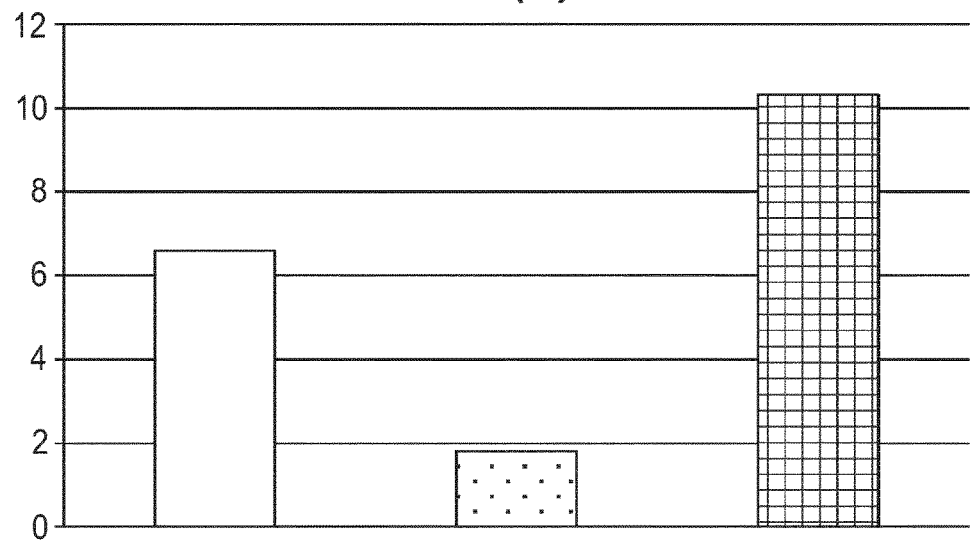
Figure 3:
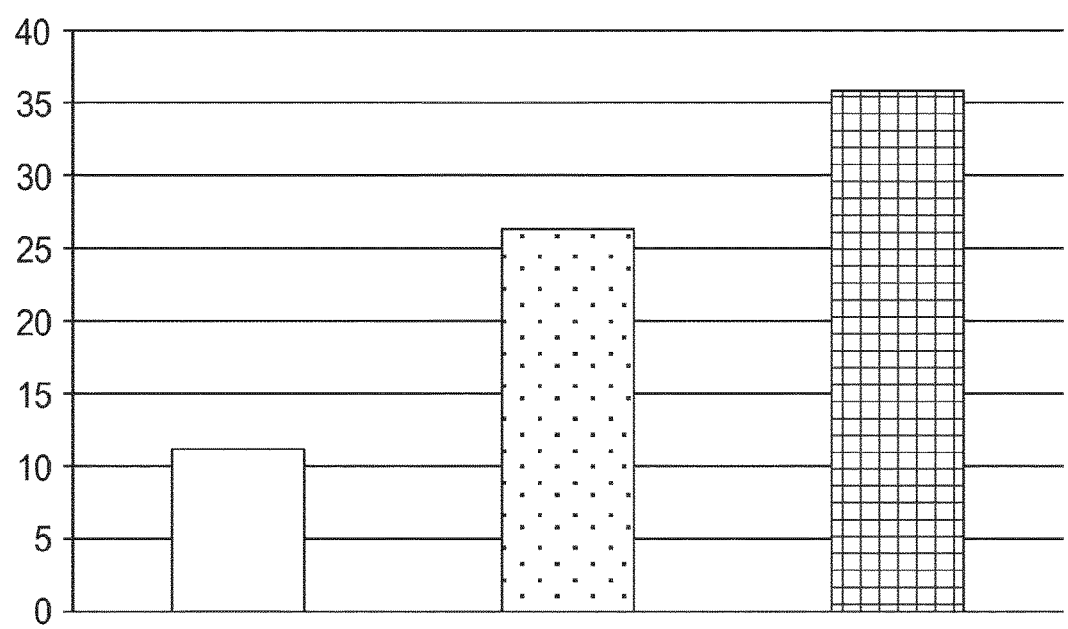
Figure 4A:
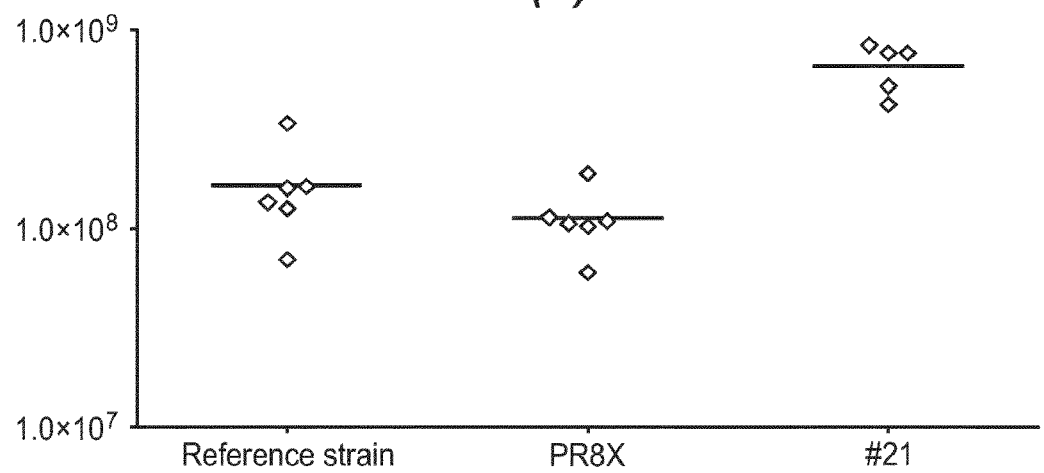
In FIG. 4(B), the white bar represents the reference vaccine strain (derived from WHO-Collaborating Centre-supplied strain), the dotted bar represents a reassortant virus containing the PR8-X backbone, and the checked bar represents a reassortant virus containing the #21 backbone. The y-axis indicates HA yield in µg/ml for pooled egg samples FIG. 5(A) and FIG. 5(B) compare virus titers (determined by FFA.
Figure 4B:
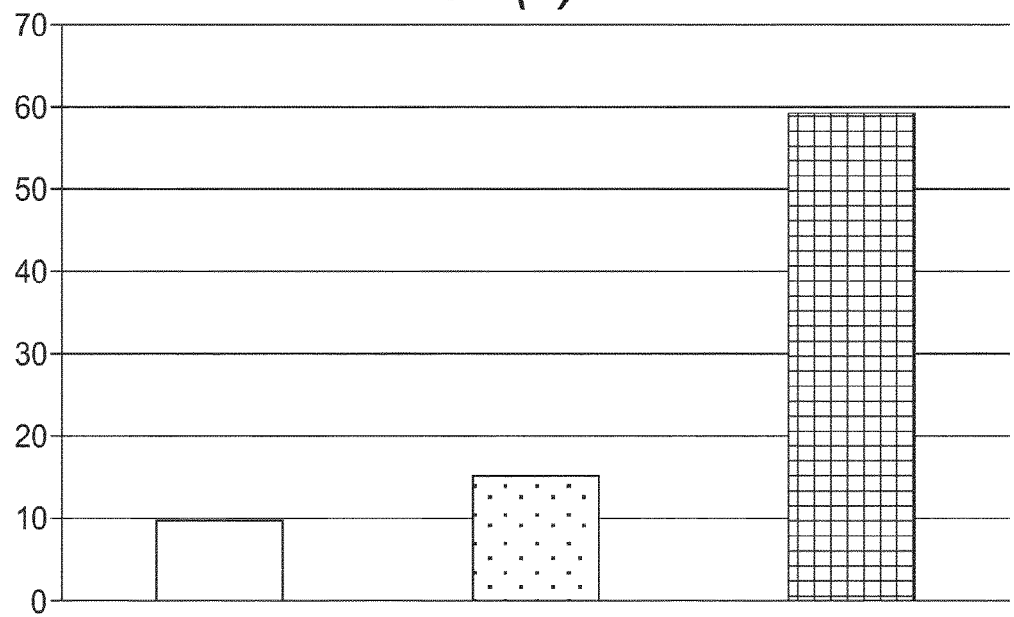

The results indicate that reassortant viruses which contain the #21 backbone consistently give higher viral titres and HA yields compared with the control virus and the virus which contains all backbone segments from PR8-X in both eggs and cell culture. This difference is due to the PB1 segment because this is the only difference between #21 reassortants and PR8-X reassortants (see FIG. 1(A), FIG. 1(B), FIG. 2(A), FIG. 2(B), FIG. 3, FIG. 4(A), and FIG. 4(B)).

Growth Characteristics of Reassortant Viruses Containing PR8-X or Canine Adapted PR8-X Backbones In order to test the effect of canine-adapted mutations on the growth characteristics of PR8-X, the inventors introduce mutations into the PA segment (E327K, N444D, and N675D), or the NP segment (A27T, E375N) of PR8-X. These backbones are referred to as PR8-X(cPA) and PR8-X(cNP), respectively. Reassortant influenza viruses are produced containing the PRB-X(cPA) and PR8-X(cNP) backbones and the HA and NA segments of a pandemic-like H1 influenza strain (strain 1) or a H3 influenza strain (strain 2). As a control a reference vaccine strain which does not contain any backbone segments from PR8-X is used. The reassortant influenza viruses are cultured in MDCK cells.

Figure 8A:
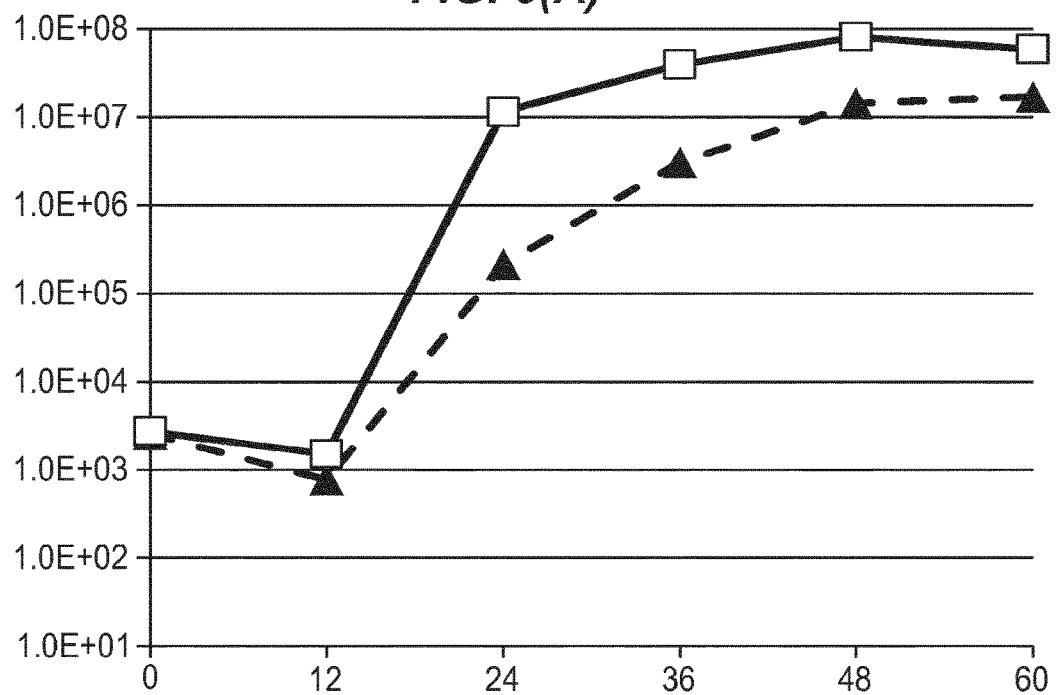
FIG. 8(A) and FIG. 8(B) compare infectious titers (determined by FFA) of viruses harvested at different time points post-infection of MDCK cells infected with reverse genetics-derived 6:2 reassortants made with either a PR8-X backbone or a modified PR8-X backbone containing canine-adapted polymerase mutations and the HA and NA segments from a pandemic-like H1 strain (strain 1).
Figure 8B:
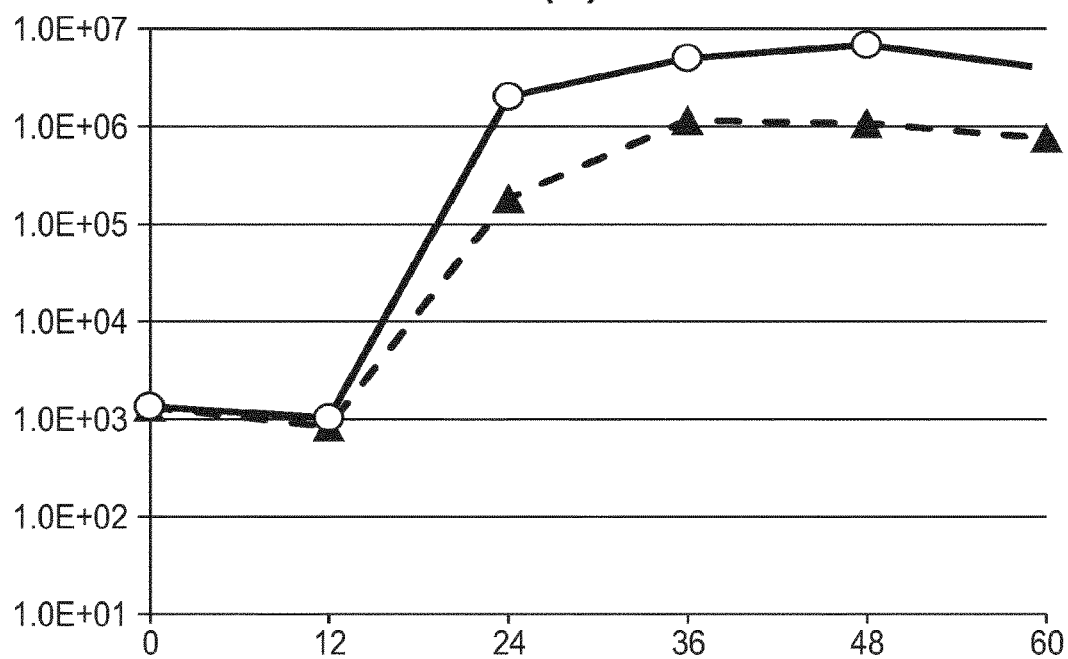
Figure 9A:
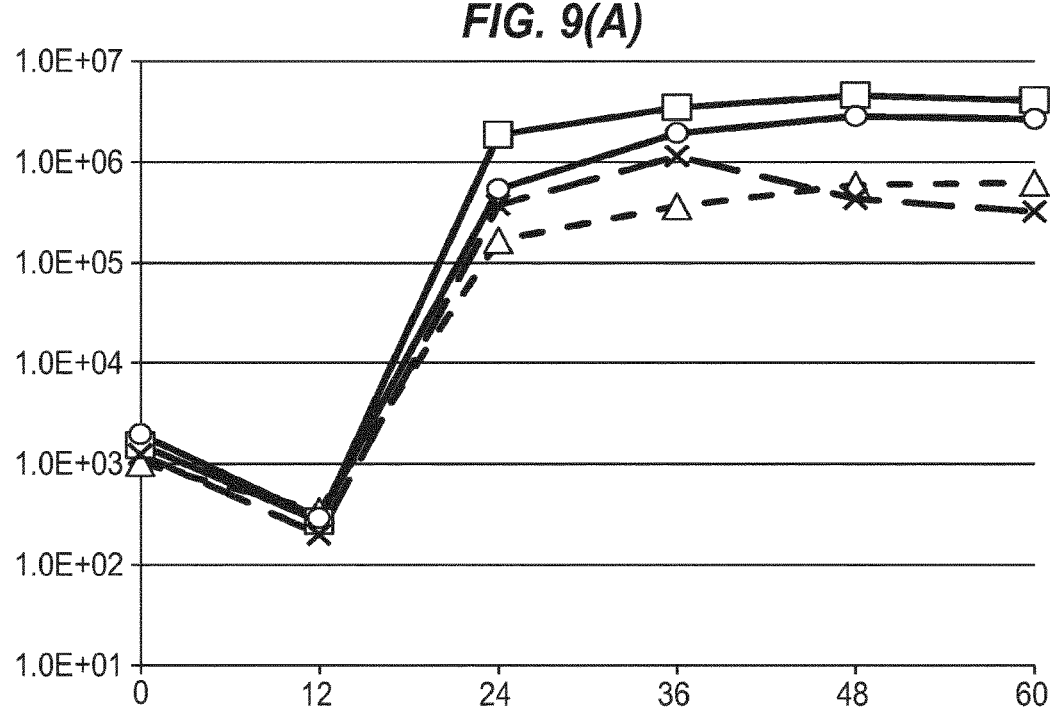
FIG. 9(A) and FIG. 9(B) compare infectious titers (determined by FFA.
Figure 9B:
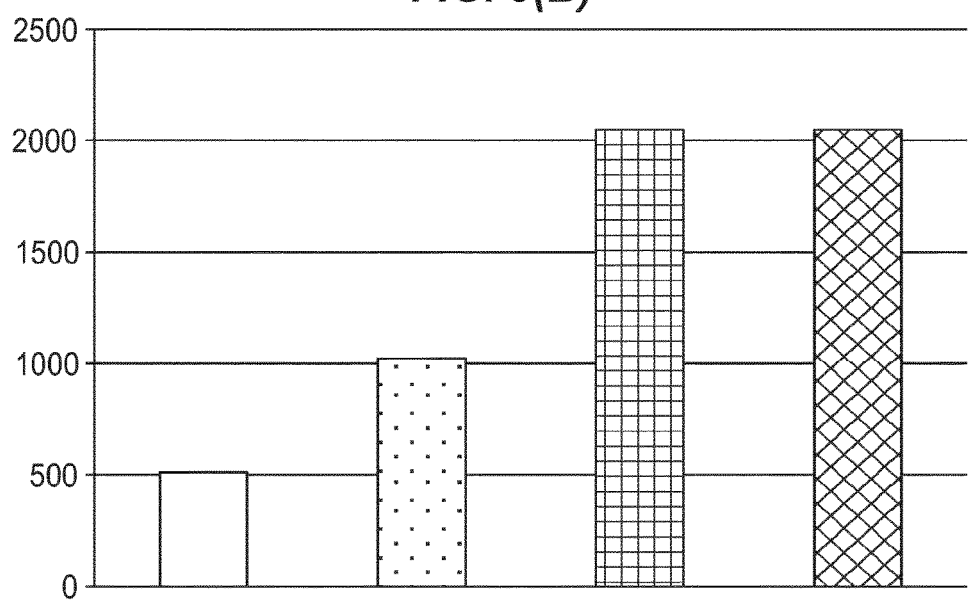
Figure 10A:
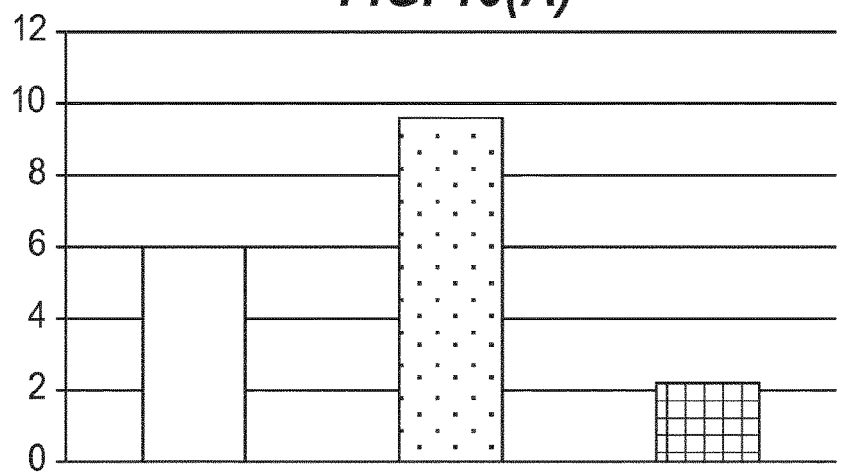
FIG. 10(A), FIG. 10(B), and FIG. 10(C) compare the HA content (determined by lectin-capture ELISA) of sucrose gradient-purified viruses harvested at 60 h post-infection from MDCK cell cultures infected with reverse genetics-derived 6:2 reassortants containing either the PR8-X or #21 backbone with the HA and NA segments from an H3 (strain 2.
Figure 10B:
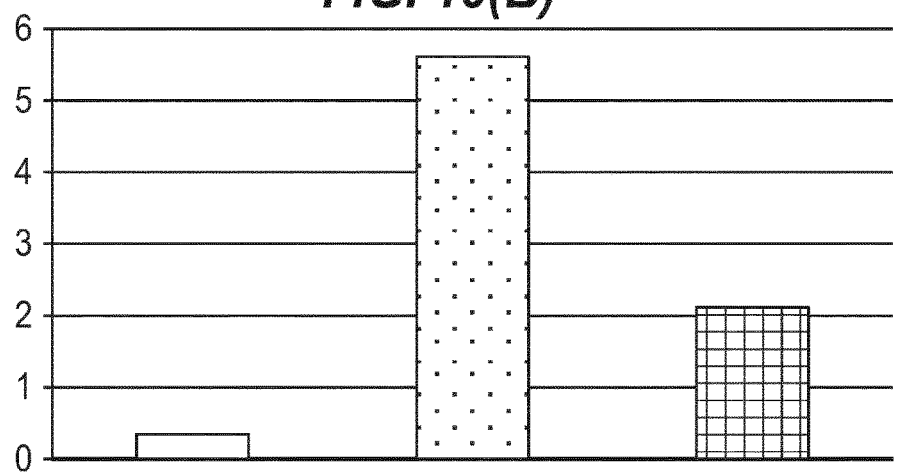
Figure 10C:
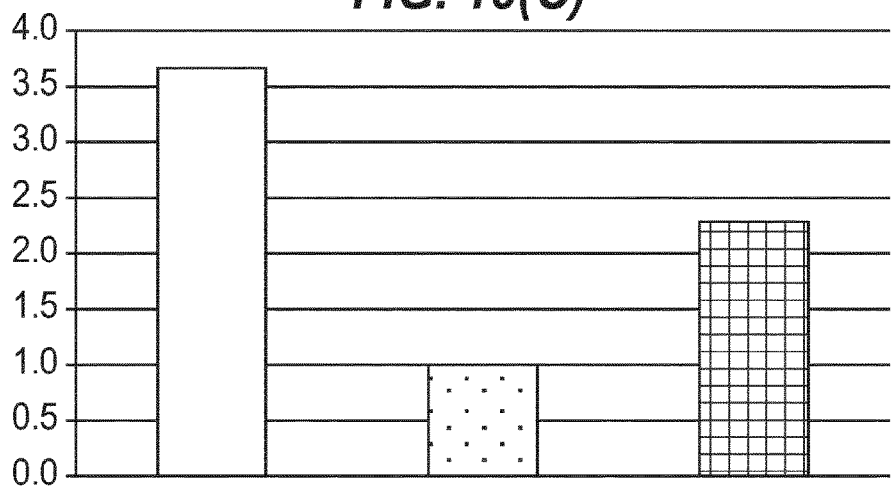

The results show that reassortant influenza viruses which contain canine-adapted backbone segments consistently grow to higher viral titres compared with reassortant influenza viruses which contain unmodified PR8-X backbone segments (see FIG. 8(A), FIG. 8(B), FIG. 9(A), and FIG. 9(B)).

Growth Characteristics of Reassortant Viruses Containing PR8-X, #21 or #21C Backbones In order to test whether canine-adapted mutations in the backbone segments improve the growth characteristics of the #21 backbone, the inventors modify the #21 backbone by introducing mutations into the PR8-X PB2 segment (R389K, T559N). This backbone is referred to as #21C. Reassortant influenza viruses are produced by reverse genetics which contain the HA and NA proteins from two different pandemic-like H1 strains (strains 1 and 2) and the other viral segments from either PR8-X, the #21 backbone or the #21C backbone. As a control a reference vaccine strain which docs not contain any backbone segments from PR8-X or A/California/07/09 is used. These viruses are cultured in MDCK cells. The virus yield of these reassortant viruses is determined. For reassortant influenza viruses containing the HA and NA segments from the pandemic-like H1 strain (strain 1) and the PR8-X or #21C backbones the FIA titres are also determined.

Figure 5A:
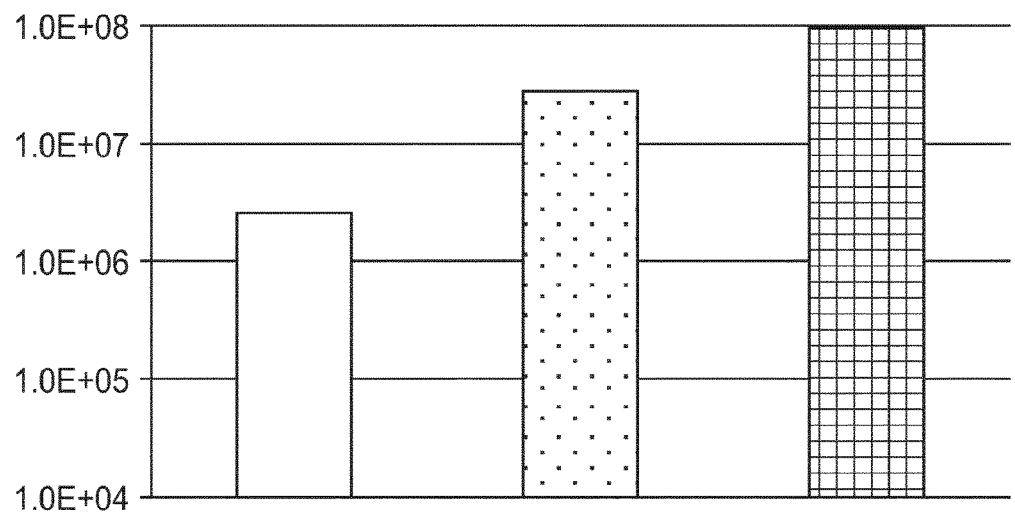
FIG. 5(A)) and HA titers (determined by lectin-capture ELISA.
Figure 5B:
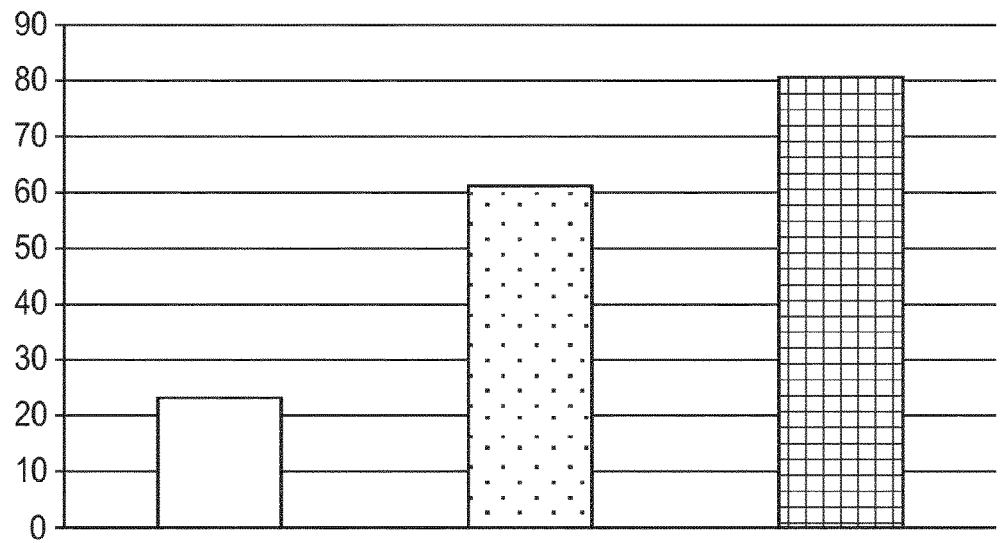
FIG. 5(B)) from viruses harvested at 60 h post-infection from MDCK cells infected with a reference vaccine strain or reverse genetics-derived 6:2 reassortant viruses made with either the #21 or #21C backbone and the HA and NA segments from a pandemic-like H1 strain (strain 2). In both figures, the white bar represents a reference vaccine strain (derived from WHO-Collaborating Centre-supplied strain) as control, the dotted bar represents a reassortant virus made with the #21 backbone, and the checked bar represents a reassortant virus made with a modified #21 backbone (#21C) containing two canine-adapted mutations (R389K, T559N) in the PR8-X PB2 segment that comprises the backbone. The y-axis in FIG. 5(A) and FIG. 5(B) indicates infectious units/ml and HA yield in µg/ml, respectively.
Figure 6:
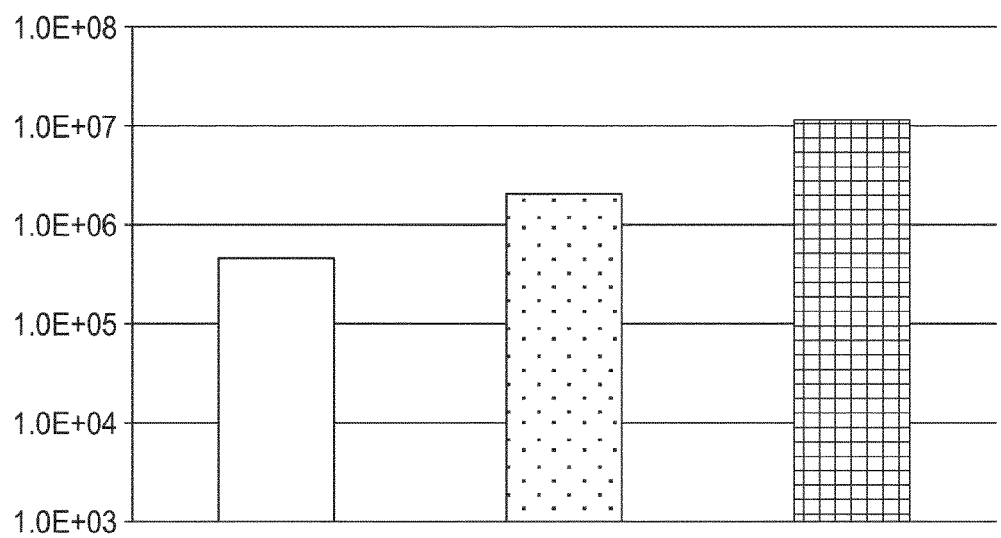
FIG. 6 compares virus titers (determined by FFA) from viruses harvested at 60 h post-infection from MDCK cells infected with reverse genetics-derived 6:2 reassortant viruses made with either the PR8-X, #21 or #21C backbone and the HA and NA segments from a different pandemic-like H1 strain (strain 1). The white bar represents the PR8-X backbone, the dotted bar represents the #21 backbone, and the checked bar represents the #21C backbone containing two canine-adapted mutations (R389K, T559N) in the PR8-X PB2 segment that comprises the backbone. The y-axis indicates infectious units/ml.
Figure 7:
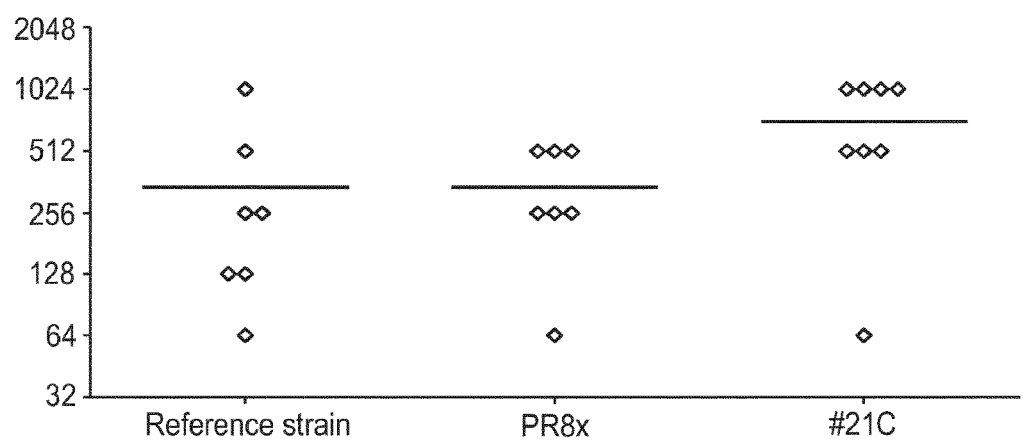
FIG. 7 compares HA titers (determined by red blood cell hemagglutination assay) from viruses harvested at 60 h post-infection from embryonated chicken eggs infected with a reference vaccine strain (derived from WHO-Collaborating Centre-supplied strain) or reverse genetics-derived 6:2 reassortant viruses containing either the PR8-X or #21C backbone and the HA and NA segments from a pandemic-like H1 strain (strain 1). The individual dots represent data from a single egg. The line represents the average of the individual data points. The y-axis indicates HA units.

The results show that reassortant influenza viruses which contain the #21C backbone consistently grow to higher viral titres compared with reassortant influenza viruses which contain only PR8-X backbone segments or the #21 backbone (see FIG. 5(A), FIG. 5(B), FIG. 6, and FIG. 7). Reassortant influenza viruses comprising the #21C backbone also show higher HA titres compared with PR8-X reassortants.

It will be understood that the invention has been described by way of example only and modifications may be made whilst remaining within the scope and spirit of the invention.

REFERENCES

[1] WO2007/002008
[2] WO2007/124327
[3] WO2010/070098
[4] Needleman & Wunsch (1970) *J. Mol. Biol.* 48, 443-453.
[5] Rice et al. (2000) *Trends Genet* 16:276-277.
[6] U.S. Pat. No. 6,468,544.
[7] Herloeher ei al. (2004) *J Infect Dis* 190(9): 1627-30.
[8] Le et al. (2005) *Nature* 437(7062): 1108.
[9] Neumann et al. (2005) Proc Natl Acad Sci USA 102: 16825-9
[10] WO2010/133964
[11] WO2009/000891
[12] U.S. provisional application No. 61/273,151
[13] Sambrook et al. Molecular Cloning: A Laboratory Manual, 2 ed., 1989, Cold Spring Harbor Press, Cold Spring Harbor, N. Y
[14] WO201 1/012999
[15] Kistner et al. (1998) Vaccine 16:960-8.
[16] Kistner et al. (1999) Dev Biol Stand 98: 101-1 10.
[17] Briilil et al. (2000) Vaccine 19: 1149-58.
[18] Pau et al. (2001) Vaccine 19:2716-21.
[19] http://www.atcc.org/
[20] http://locus.umdnj.edu/
[21] WO97/37000.
[22] Brands et al. (1999) Dev Biol Stand 98:93-100.
[23] Halperin et al. (2002) Vaccine 20: 1240-7. [24] EP-A-1260581 (WOO 1/64846)
[25] WO2006/071563
[26] WO2005/113758
[27] WO97/37001
[28] WO02/28422.
[29] WO02/067983.
[30] WO02/074336.
[31] WOOI/21 151.
[32] WO02/097072.
[33] WO2005/113756.
[34] Huckriede et al. (2003) *Methods Enzymol* 373:74-91.
[35] Vaccines, (eds. Plotkins & Orenstein). 4th edition, 2004, ISBN: 0-7216-9688-0
[36] Treanor et al. (1996) *J Infect Dis* 173: 1467-70.
[37] Keitel et al. (1996) *Clin Diagn Lab Immunol* 3:507-10.
[38] Herlocher et al. (2004) *J Infect Dis* 190(9): 1627-30.
[39] Le et al. (2005) *Nature* 437(7062): 1108.
[40] WO2008/068631.
[41] Gennaro (2000) Remington: The Science and Practice of Pharmacy. 20th edition, ISBN: 0683306472.
[42] Banzhoff (2000) *Immunology Letters* 71:91-96.
[43] Nony et al. (2001) *Vaccine* 27:3645-5 1.
[44] EP-B-0870508.
[45] U.S. Pat. No. 5,948,410.

[46] WO2007/052163.
[47] WO2007/052061
[48] WO90/14837.
[49] Podda & Dei Giudice (2003) *Expert Rev Vaccines* 2:197-203.
[50] Podda (2001) *Vaccine* 19: 2673-2680.
[51] *Vaccine Design: The Subunit and Adjuvant Approach* (eds. Powell & Newman) Plenum Press 1995 (ISBN 0-306-44867-X).
[52] *Vaccine Adjuvants: Preparation Methods and Research Protocols* (Volume 42 of *Methods in Molecular Medicine* series). ISBN: 1-59259-083-7. Ed. O'Hagan.
[53] WO2008/043774.
[54] Allison & Byars (1992) *Res Immunol* 143:519-25.
[55] Hariharan et al. (1995) *Cancer Res* 55:3486-9.
[56] US-2007/014805.
[57] US-2007/0191314.
[58] S li et al. (2004) *Vaccine* 22(25-26):3464-9.
[59] WO95/11700.
[60] U.S. Pat. No. 6,080,725.
[61] WO2005/097181.
[62] WO2006/113373.
[63] Potter & Oxford (1979) *Br Med Bull* 35: 69 75.
[64] Greenbaum et al. (2004) *Vaccine* 22:2566-77.
[65] Zurbriggen et al. (2003) *Expert Rev Vaccines* 2:295-304.
[66] Piascik (2003) *J Am Pharm Assoc (Wash DC)*. 43:728-30.
[67] Mann et al. (2004) *Vaccine* 22:2425-9.
[68] Halperin et al. (1979) *Am J Public Health* 69: 1247-50.
[69] Herbert et al. (1979) *J Infect Dis* 140:234-8.
[70] Chen et al, (2003) *Vaccine* 21:2830-6.
[71] *Current Protocols in Molecular Biology* (F. M. Ausubel et at, cds., 1987) Supplement 30.
[72] Smith & Waterman (1981) *Adv. Appl. Math.* 2: 482-489

The invention claimed is:

1. A method of preparing a reassortant influenza A virus comprising:
   an HA segment, an NA segment and backbone segments PA, PBI, PB2, NP, NS and M, wherein the backbone segments are from two donor strains, wherein the PB1 segment is from the A/California/07/09 influenza strain and all other backbone segments are from the PR8-X influenza strain, further wherein the PA segment has the sequence of SEQ ID NO: 1, the PB2 segment has the sequence of SEQ ID NO: 3, the NP segment has the sequence of SEQ ID NO: 4, the M segment has the sequence of SEQ ID NO: 5, and the NS segment has the sequence of SEQ ID NO: 6,
   wherein the method comprises:
      (i) introducing into a culture host at least one expression construct which encode(s) the viral segments required to produce the reassortant influenza A virus; and
      (ii) culturing the culture host in order to produce the reassortant influenza A virus.

2. The method of claim 1, wherein the at least one expression construct comprises at least one sequence having at least 90% identity or 100% identity with the sequences of SEQ ID NOs: 9 and 11 to 14.

3. The method of claim 1, wherein the HA segment is from an H1 influenza virus.

4. A method for producing influenza viruses comprising: (a) infecting a culture host with the reassortant influenza virus of claim 1; (b) culturing the host from step (a) to produce the virus; and optionally (c) purifying the virus produced in step (b).

5. A method of preparing a vaccine, comprising: (a) preparing a virus by the method of claim 4 and (b) preparing a vaccine from the virus.

6. The method of claim 4, wherein the culture host is an embryonated hen egg.

7. The method of claim 4, wherein the culture host is a mammalian cell, optionally an MDCK, Vero or PerC6 cell.

8. The method of claim 7, wherein the cell grows adherently or in suspension.

9. The method of claim 5, wherein step (b) involves inactivating the virus.

10. The method of claim 5, wherein the vaccine is a whole virion vaccine, a split virion vaccine, a surface antigen vaccine, or a virosomal vaccine.

11. The method of claim 5, wherein the vaccine contains less than 10 ng of residual host cell DNA per dose.

12. The method of claim 5, wherein at least one of the influenza strains is of the H1, H2, H5, H7 or H9 subtype.

13. A method for producing influenza viruses, comprising infecting a culture host with a reassortant influenza A virus comprising an HA segment, an NA segment and backbone segments PA, PB1, PB2, NP, NS and M, wherein the backbone segments are from two donor strains, further wherein at least one backbone segment is from the A/California/07/09 influenza strain and:
   a) the PB2 segment comprises a lysine in the position corresponding to amino acid 389 of SEQ ID NO: 3 when aligned to SEQ ID NO: 3, using a pairwise alignment algorithm;
   b) the PB2 segment comprises an asparagine in the position corresponding to amino acid 559 of SEQ ID NO: 3 when aligned to SEQ ID NO: 3, using a pairwise alignment algorithm;
   c) the PA genome segment comprises a lysine in the position corresponding to amino acid 327 of SEQ ID NO: 1 when aligned to SEQ ID NO: 1, using a pairwise alignment algorithm;
   d) the PA segment comprises an aspartic acid in the position corresponding to amino acid 444 of SEQ ID NO: 1 when aligned to SEQ ID NO: 1, using a pairwise alignment algorithm;
   e) the PA segment comprises an aspartic acid in the position corresponding to amino acid 675 of SEQ ID NO: 1 when aligned to SEQ ID NO: 1, using a pairwise alignment algorithm;
   f) the NP segment comprises a threonine in the position corresponding to amino acid 27 of SEQ ID NO: 4 when aligned to SEQ ID NO: 4 using a pairwise alignment algorithm; or
   g) the NP segment comprises an asparagine in the position corresponding to amino acid 375 of SEQ ID NO: 4 when aligned to SEQ ID NO: 4, using a pairwise alignment algorithm.

14. The method of claim 13, comprising culturing the host to produce the virus and, optionally, purifying the virus.

15. The method of claim 14, wherein the culture host is selected from: an embryonated hen egg, a mammalian cell, optionally an MDCK, a Vero cell or a PerC6 cell.

16. A method of preparing a vaccine, comprising: (a) preparing a virus by the method of claim 14 and (b) preparing a vaccine from the virus.

17. A method for producing influenza viruses, comprising infecting a culture host with the reassortant influenza virus of claim 13, wherein:

a) the PB2 segment comprises a lysine in the position corresponding to amino acid 389 of SEQ ID NO: 3 and asparagine in the position corresponding to amino acid 559 of SEQ ID NO: 3 when aligned to SEQ ID NO: 3, using a pairwise alignment algorithm;

b) the PA segment comprises a lysine in the position corresponding to amino acid 327; aspartic acid in the position corresponding to amino acid 444 of SEQ ID NO: 1 and aspartic acid in the position corresponding to amino acid 675 when aligned to SEQ ID NO: 1, using a pairwise alignment algorithm;

c) the NP genome segment comprises a threonine in the position corresponding to amino acid 27 of SEQ ID NO: 4 and asparagine in the position corresponding to amino acid 375 when aligned to SEQ ID NO: 4, using a pairwise alignment algorithm; or d) the influenza A strain is a H1 strain.

18. The method of claim 17, comprising culturing the host to produce the virus and, optionally, purifying the virus.

19. The method of claim 18, wherein the culture host is selected from: an embryonated hen egg, a mammalian cell, optionally an MDCK, a Vero cell or a PerC6 cell.

20. A method of preparing a vaccine, comprising: (a) preparing a virus by the method of claim 18 and (b) preparing a vaccine from the virus.

21. The method of claim 7, wherein the MDCK cell is MDCK 33016 (DSM ACC2219).

22. The method of claim 15, wherein the MDCK cell is MDCK 33016 (DSM ACC2219).

23. The method of claim 19, wherein the MDCK cell is MDCK 33016 (DSM ACC2219).

* * * * *

UNITED STATES PATENT AND TRADEMARK OFFICE
CERTIFICATE OF CORRECTION

PATENT NO. : 10,500,266 B2
APPLICATION NO. : 15/621270
DATED : December 10, 2019
INVENTOR(S) : Peter Mason et al.

Page 1 of 1

It is certified that error appears in the above-identified patent and that said Letters Patent is hereby corrected as shown below:

On the Title Page

Item (73), Lines 2-3:
"Synthetic Genomics, Inc., La Lolla, CA (US)" should read --Synthetic Genomics, Inc., La Jolla, CA (US)--.

Signed and Sealed this
Eleventh Day of February, 2020

Andrei Iancu
*Director of the United States Patent and Trademark Office*